United States Patent
Sakasegawa et al.

(10) Patent No.: US 11,773,379 B2
(45) Date of Patent: Oct. 3, 2023

(54) ENZYMES AND REAGENTS FOR MEASUREMENT OF SHORT CHAIN FATTY ACIDS

(71) Applicant: SYSMEX CORPORATION, Kobe (JP)

(72) Inventors: Shinichi Sakasegawa, Tokyo (JP); Kenji Konishi, Tokyo (JP); Yasushi Shirahase, Kobe (JP); Toshiyuki Yoshida, Kobe (JP)

(73) Assignee: SYSMEX CORPORATION, Kobe (JP)

(*) Notice: Subject to any disclaimer, the term of this patent is extended or adjusted under 35 U.S.C. 154(b) by 0 days.

(21) Appl. No.: 17/221,008

(22) Filed: Apr. 2, 2021

(65) Prior Publication Data

US 2021/0222227 A1    Jul. 22, 2021

Related U.S. Application Data

(63) Continuation of application No. PCT/JP2019/040043, filed on Oct. 10, 2019.

(30) Foreign Application Priority Data

Oct. 19, 2018  (JP) .............................. JP2018-197564

(51) Int. Cl.
   *C12N 9/12*  (2006.01)
   *C12Q 1/48*  (2006.01)

(52) U.S. Cl.
   CPC ........... *C12N 9/1217* (2013.01); *C12Q 1/485* (2013.01)

(58) Field of Classification Search
   CPC .................................................. C12N 9/1217
   See application file for complete search history.

(56) References Cited

U.S. PATENT DOCUMENTS

| | | | |
|---|---|---|---|
| 5,916,761 A | 6/1999 | Koga et al. | |
| 10,472,665 B2 | 11/2019 | Ueda et al. | |
| 2017/0306389 A1 | 10/2017 | Ueda et al. | |
| 2018/0371503 A1 | 12/2018 | Allard et al. | |

FOREIGN PATENT DOCUMENTS

| | | | | |
|---|---|---|---|---|
| JP | 09-285297 A | | 11/1997 | |
| JP | 2009-229456 A | | 10/2009 | |
| WO | WO 2011136063 | * | 3/2011 | ............... C12Q 1/48 |
| WO | 2016/047580 A1 | | 3/2016 | |
| WO | 2017/085167 A2 | | 5/2017 | |

OTHER PUBLICATIONS

Twarog et al, Enzymatic Phosphorylation of Butyrate. J. Biol Chem. vol 237, No. 8, 1962 p. 2474-2477.*
Noda et al, 2011, Method for measurement of speci c substance, and kit for measurement of speci c substance. Machine English translation of WO 2011136063.*
Fonknechten et al, Clostridium sticklandii, a specialist in amino acid degradation:revisiting its metabolism through its genome sequence. BMC Genomics 2010, 11:555.*
UniProt Acc#E3PVP7 from Fonknechten et al, BMC Genomics 2010, 11:555. Alignment with SID17.*
Noda et al, 2011 Method for measurement of speci c substance, and kit for measurement of speci c substance. English machine translation of WO 2011136063.*
K. Ochiai et al., "Effects on Periodontal and Systemic Diseases of Butyric Acid Produced by Periodontopathic Bacteria", Journal of Intestinal Microbiology, 2014, pp. 111-120, vol. 28, No. 3.
K. Ochiai et al., "Research on short-chain fatty acids in the oral cavity has revealed; Tissue-damaging effects of Metabolites of anaerobic bacteria and butyric acid and Epigenetics", Journal of Japanese Pharmacology (Folia Pharmacologica Japonica), pp. 81-87, 2014, vol. 144.
International Search Report of PCT/JP2019/040043 dated Dec. 10, 2019 [PCT/ISA/210].
Notice of Reasons for Refusal dated Aug. 8, 2023 issued by the Japanease Patent Office in JP application No. 2020-553130.

* cited by examiner

*Primary Examiner* — Yong D Pak
(74) *Attorney, Agent, or Firm* — Sughrue Mion, PLLC

(57) ABSTRACT

Disclosed are methods and reagents for the enzymatic measurement of short-chain fatty acids, having 3 to 6 carbon atoms, in a sample. Methods include the use of recombinant butyrate kinases from multiple species, combined various reagents that includes ATP, to detect butyric acid in different types of samples via measurement of ATP consumption. Disclosed also are the reagents themselves.

9 Claims, 10 Drawing Sheets

Specification includes a Sequence Listing.

FIG. 5

```
      1  2  (kDa)
         — 97.2
         — 66.4
→        — 45.0
         — 29.0
         — 20.1
         — 14.3
```

FIG. 6

```
      1  2  (kDa)
         — 97.2
         — 66.4
         — 45.0
→        — 29.0
         — 20.1
         — 14.3
```

FIG. 7

```
      1  2  (kDa)
         — 97.2
         — 66.4
→        — 45.0
         — 29.0
         — 20.1
         — 14.3
```

ENZYMES AND REAGENTS FOR MEASUREMENT OF SHORT CHAIN FATTY ACIDS

CROSS REFERENCE TO RELATED APPLICATIONS

This application is a Continuation of International Application No. PCT/JP2019/040043 filed on Oct. 10, 2019, claiming priority based on Japanese Patent Application No. 2018-197564, filed on Oct. 19, 2018, entitled "ENZYMATIC MEASUREMENT METHOD AND REAGENT FOR ENZYMATIC MEASUREMENT", the entire contents of which are incorporated herein by reference.

FIELD OF THE INVENTION

The present invention relates to an enzymatic measurement method and a reagent for enzymatic measurement.

BACKGROUND

Butyric acid is naturally present in a milk fat such as butter in the form of a glycerin ester. Butyric acid is also produced by butyric acid fermentation of saccharides by a butyric-acid bacterium. In recent years, attention has been paid to the role of butyric acid in a living body. For example, butyric acid produced by a gut flora attracts attention as a substance that is appropriately diluted in a mucin layer and induces the differentiation of a T cell into a regulatory T cell. Butyric acid has beneficial effects on the intestinal environment at a moderately low concentration, such as being absorbed by an intestinal mucosal epithelium and becoming an energy source to promote the growth of the mucosal epithelium. Butyric acid in food also attracts attention because the beneficial effect of butyric acid can be obtained not only by butyric acid produced by a bacterium in a living body but also by oral administration of butyric acid. Butyric acid is also present in saliva, but it has been reported that there is no mucin layer in an oral cavity, so that the concentration of butyric acid becomes high and damages a cell. On the other hand, it is known that the order of cytotoxicity is butyric acid>valeric acid>propionic acid among the same short-chain fatty acids, and that acetic acid does not show cytotoxicity until a high concentration (Xiaolan Yu, et al; Short-chain fatty acids from periodontal pathogens suppress histone deacetylases, EZH2, and SUV39H1 to promote Kaposi's sarcoma associated herpesvirus replication.2014, Vol. 88, No. 9, 4466-4479.)

As an enzymatic measurement method of a fatty acid, a method using acyl-CoA synthetase (ACS:EC 6.2.1.) is well known. A reagent capable of visible part measuring a fatty acid in serum by combining acyl-CoA synthetase (EC 6.2.1.3) with acyl-CoA oxidase and peroxidase (POD) is commercially available. However, it has been reported that EC 6.2.1.3 reacts with a fatty acid higher than a medium-chain fatty acid and does not react with butyric acid, propionic acid, and acetic acid (Kohei Hosaka, et al., A New Colorimetric method for the determination of free fatty acids with acyl-CoA synthetase and acyl-CoA oxidase. J Biochem. 1981, 89, 1799-1803). On the other hand, it has been reported that EC 6.2.1.2 works only on a short-chain fatty acid and has high reactivity with acetic acid and propionic acid and does not react with butyric acid (Catherine AR. et al. Regulation of volatile fattyacid uptake by mitochondrial Acyl CoA Synthetase of Bovine Heart. J Dairy Sci. 1981, 64:2336-2343.). As described above, the demand for measuring butyric acid contained in a biological sample and food is increasing, and currently, the measurement of butyric acid is performed by a gas chromatography-mass spectrometer (GC-MS) or a high-performance liquid chromatography (HPLC). For example, Japanese Laid-Open Patent Publication No. 2009-229456 discloses that short-chain fatty acids such as butyric acid in feces were measured by HPLC. The advantage of the GC-MS is that it can separate acetic acid and butyric acid with different functions.

However, measurement by the GC-MS and the HPLC requires an expensive device and is complicated to operate. Therefore, there is a need for a technique that makes it possible to easily measure a short-chain fatty acid containing butyric acid without being affected by acetic acid.

SUMMARY OF THE INVENTION

The scope of the present invention is defined solely by the appended claims, and is not affected to any degree by the statements within this summary.

The present inventors found that butyric acid in a sample can be measured without being affected by acetic acid by producing adenosine diphosphate (ADP) from butyric acid and adenosine triphosphate (ATP) in the sample by the action of butyrate kinase, and by measuring the produced ADP. That is, the present inventors completed the present invention by establishing a novel enzymatic measurement method capable of measuring butyric acid in a sample.

Therefore, the present invention provides an enzymatic measurement method including contacting butyric acid in a sample, ATP, and butyrate kinase to produce ADP, and measuring the produced ADP. Further, the present invention provides an enzymatic measurement method including contacting a short-chain fatty acid having 3 to 6 carbon atoms in a sample, ATP, and butyrate kinase to produce ADP, and measuring the produced ADP. Furthermore, the present invention provides a reagent for enzymatic measurement including butyrate kinase and ATP.

The present invention makes it possible to easily measure butyric acid in a sample. The present invention is useful as an assistance in a diagnosis of periodontal disease.

BRIEF DESCRIPTION OF THE DRAWINGS

FIG. 5 is a diagram showing the result of analysis of a solution of recombinant butyrate kinase derived from *Acetoanaerobium sticklandii* by SDS-PAGE;

FIG. 6 is a diagram showing the result of analysis of a solution of recombinant butyrate kinase derived from *Thermosediminibacter oceani* by SDS-PAGE;

FIG. 7 is a diagram showing the result of analysis of a solution of recombinant butyrate kinase derived from *Thermosediminibacter oceani* by SDS-PAGE;

DETAILED DESCRIPTION OF THE PREFERRED EMBODIMENTS

Figure 1:
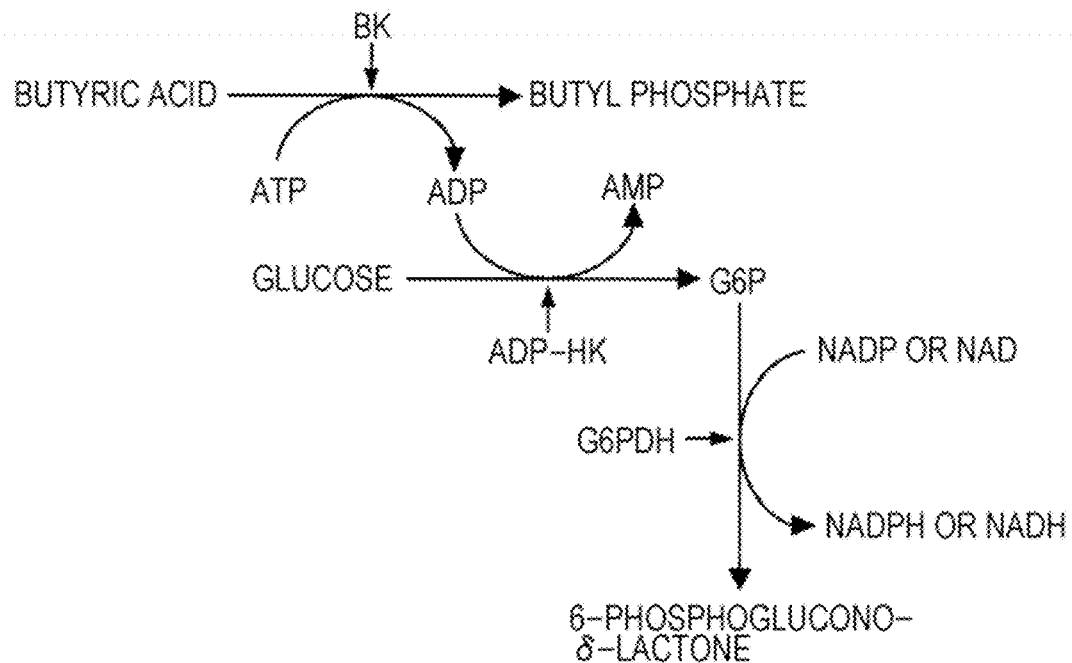
FIG. 1 is a diagram showing a pathway when reactions catalyzed by each of butyrate kinase, ADP dependent hexokinase (ADP-HK), and glucose-6-phosphate dehydrogenase (G6PDH) are carried out in the same reaction system.

As used herein, "measuring" includes determining a value of the amount or concentration of a target substance, and obtaining a measurement result reflecting the amount or concentration of a target substance. The measurement result may be any of qualitative information, quantitative information, and semi-quantitative information. The qualitative information refers to information indicating the presence or absence of the target substance. The quantitative information refers to numerical values such as a measured value obtained by a measuring device. Based on the quantitative information, the value of the amount or concentration of the target substance can be determined. The semi-quantitative information refers to information indicating the amount or concentration of the target substance in stages by a word, a number, a color, etc. For example, as the semi-quantitative information, words such as "below a detection limit", "little", "medium", and "much" may be used. The "measurement result reflecting the amount or concentration of the target substance" means an index that changes according to the amount or concentration of the target substance. The index is preferably a visible or mechanically measurable optical change. Specifically, the absorbance, turbidity, coloring, etc. of a reaction solution are exemplified.

[1. Enzymatic Measurement Method of Butyric Acid]

In the enzymatic measurement method of the present embodiment (hereinafter, also simply referred to as "method"), first, butyric acid in a sample is contacted ATP and butyrate kinase to produce ADP. As used herein, the term "butyric acid" includes not only butyric acid, but also isobutyric acid which is an isomer of butyric acid. Butyric acid in the sample may be in a salt or ionic state. Examples of butyrate include an alkali metal salt and a calcium salt. Specific examples of the alkali metal salt include sodium butyrate, lithium butyrate, and sodium isobutyrate.

The sample is not particularly limited as long as it may contain butyric acid, butyrate, or butyrate ion. Examples of the sample include a biological sample and a food and drink. Examples of the biological sample include saliva, gingival crevicular fluid, blood, plasma, serum, milk, urine, and feces. Examples of the food and drink include dairy products such as milk. The sample may be diluted with a suitable solvent. A culture supernatant of a microorganism that produces butyric acid may be used as the sample.

The sample is preferably liquid, as the reaction with butyrate kinase is usually carried out in liquid. The liquid sample is not limited to a solution, but also includes a suspension, sol, etc. in which fine solid substances such as cells are suspended. For example, when the sample is solid, the sample may be crushed and dissolved or suspended in an appropriate solvent, and then the solid substance may be removed by centrifugation or filtration to prepare a liquid sample. When liquid samples such as saliva contain an insoluble impurity, the sample may be centrifuged or filtered to remove the insoluble impurity.

The solvent can be appropriately selected from an aqueous solvent generally used in the field of biochemistry. Examples of such a solvent include water, physiological saline, and a buffer. The buffer preferably has a pH of 6 or more and 10 or less. Examples of the buffer include Good buffers such as MES, PIPES, BES, TES, HEPES, and CHES, Tris hydrochloride acid buffer (Tris-HCl), phosphate-buffered saline (PBS), and imidazole hydrochloride buffer. Butyrate kinase has little reaction to acetic acid, but large amounts of acetic acid cause a blank rise in the reagent over time, affecting reagent stability. Therefore, it is preferable not to use a buffer containing acetic acid or acetate.

Butyrate kinase (ATP: butanoate 1-phosphotransferase or EC 2.7.2.7) is an enzyme that catalyzes the reaction represented by the following formula (1). Butyrate kinase itself is known, for example, as one of the metabolic enzymes of a *Clostridium* bacterium involved in acetone-butanol fermentation. The amino acid sequence of butyrate kinase and the base sequence of the gene encoding butyrate kinase can be obtained from a known database.

[Chemical formula 1]

Butyric acid+ATP 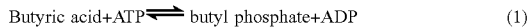 butyl phosphate+ADP        (1)

Butyrate kinase may be of natural origin or may be an enzyme artificially obtained by a gene recombination technique or the like. In the present embodiment, butyrate kinase may have one or more amino acid residues deleted, substituted, or added to the amino acid sequence of butyrate kinase of natural origin as long as it has an action of catalyzing the above reaction.

The origin of butyrate kinase is not particularly limited. A gene encoding butyrate kinase can be cloned from microorganisms such as, *Acetoanaerobium sticklandii* (also known as *Clostridium sticklandii*), *Thermosediminibacter oceani*, *Natranaerobius thermophilus*, and *Symbiobacterium thermophilum*. These microorganisms and their chromosomal DNA are generally available, and can be purchased, for example, from Deutsche Sammlung von Mikroorganismen and Zellkulturen GmbH (DSMZ). In the present embodiment, it is preferable to use butyrate kinase derived from *Acetoanaerobium sticklandii* or *Thermosediminibacter oceani*. More preferably, a thermophilic bacterium, for example, butyrate kinase derived from *Thermosediminibacter oceani* is used. Butyrate kinase derived from *Acetoanaerobium sticklandii* includes, for example, the amino acid sequence represented by SEQ ID NO: 17. Butyrate kinase derived from *Thermosediminibacter oceani* includes, for example, the amino acid sequence represented by SEQ ID NO: 19.

The final concentration of butyrate kinase in a mixed solution of a sample, butyrate kinase, and ATP (hereinafter, also referred to as "reaction mixed solution") is not particularly limited. The lower limit of the final concentration of butyrate kinase in the reaction mixed solution may be, for example, 0.01 U/mL or more, preferably 0.1 U/mL or more, further preferably 0.5 U/mL or more, and the upper limit of the final concentration may be, for example, 150 U/mL or less, preferably 50 U/mL or less, and further preferably 20 U/mL or less. These values may differ depending on measurement conditions such as the reagent composition, temperature, measurement wavelength, and sub-wavelength. The final concentration of butyrate kinase is preferably low from the viewpoint of economy, etc. and preferably high from the viewpoint of the shelf life of a reagent. "U/mL" is an unit of the enzyme activity value. One U of butyrate kinase is defined as the amount of enzyme that phosphorylates 1 µmol of butyric acid per minute. The method itself for measuring the enzyme activity value is known, and a person skilled in the art can easily measure the activity value by a routine experiment.

The enzymatic reaction represented by the above formula (1) is a reversible reaction, but in the present embodiment, by adding enough ATP, the enzymatic reaction proceeds toward the production of butyl phosphate and ADP. The amount of ATP added is not particularly limited. In the present embodiment, the lower limit of the final concentration of ATP in the reaction mixed solution at the start of the enzymatic reaction may be, for example, 0.1 mM or more, preferably 0.2 mM or more, further preferably 0.5 mM or more, and the upper limit of the final concentration may be, for example, 50 mM or less, preferably 10 mM or less, and further preferably 5 mM or less.

In the present embodiment, it is preferable to contact the sample, ATP, and butyrate kinase in the presence of a divalent metal ion from the viewpoint of more efficiently performing the enzymatic reaction by butyrate kinase. Examples of the divalent metal ion include a magnesium ion and a zinc ion. Among them, the magnesium ion is particularly preferable. The divalent metal ion can be supplied by adding a compound forming the divalent metal ion or an aqueous solution thereof to a mixed solution of a sample, ATP, and butyrate kinase. The amount of the divalent metal ion added is not particularly limited. The lower limit of the final concentration of the divalent metal ion in the reaction mixed solution at the start of the enzymatic reaction may be, for example, 0.1 mM or more, preferably 0.5 mM or more, further preferably 1 mM or more, and the upper limit of the final concentration is, for example, may be 50 mM or less, preferably 20 mM or less, further preferably 10 mM or less. The amount of the divalent metal ion used under the above conditions is, for example, in the case of a magnesium ion, the lower limit is 0.1 equivalents or more, preferably 0.5 equivalents or more, and further preferably 1 equivalent or more with respect to the concentration of ATP, and the upper limit is 10 equivalents or less, preferably 5 equivalents or less, and further preferably 3 equivalents or less. The most preferred concentration is 1 equivalent of ATP.

The compound forming the divalent metal ion is not particularly limited as long as the compound produces the divalent metal ion in a suitable solvent and the anion generated from the compound does not inhibit the enzymatic reaction. As such a compound, a salt of the divalent metal and an inorganic acid is preferable, and examples of the compound include a salt of acids such as hydrochloric acid, sulfuric acid, and nitric acid and the divalent metal. Examples of the divalent metal salt include, more preferably, a salt of at least one metal selected from the group consisting of magnesium, zinc, and the like. The compound forming the divalent metal ion may be an anhydride or a hydrate.

If necessary, the sample, ATP, and butyrate kinase may be contacted in the presence of a surfactant. The surfactant can be appropriately selected from a nonionic surfactant, a cationic surfactant, an anionic surfactant, and an amphoteric surfactant. Among them, the nonionic surfactant are preferable, and polyoxyethylene alkylphenyl ether-based nonionic surfactant or polyoxyethylene alkyl ether-based nonionic surfactant are particularly preferable. Examples of such nonionic surfactant include Triton (registered trademark) X-100, TN-100 (ADEKA Corporation), EMULGEN 1150s-60 (Kao Corporation), and Newcol 710 (NIPPON NYUKAZAI CO., LTD.).

In the method of the present embodiment, the ADP produced by a reaction catalyzed by butyrate kinase is measured. As shown in the formula (1), the amount of ADP produced is proportional to the amount of butyric acid which is a substrate of butyrate kinase. Therefore, the produced ADP can be measured to measure butyric acid in the sample. That is, the method of the present embodiment can be said to be a method for measuring butyric acid in a sample based on the measurement result of ADP produced by contacting the sample, ATP, and butyrate kinase. In the present embodiment, the amount or concentration of the butyric acid in the sample can be determined based on the measured value reflecting the amount or concentration of the produced ADP (hereinafter, also referred to as "measured value of ADP"). For example, a calibration curve showing the relation between the measured value of ADP and the butyric acid concentration is created by measuring the butyric acid aqueous solution having a known concentration in the same manner as the sample. The value of the butyric acid concentration in the sample can be determined from the measured value of ADP in the reaction mixed solution using the obtained calibration curve. The butyric acid aqueous solution having a known concentration can be used as a calibration reagent, and conditions such as the butyric acid concentration in the calibration reagent, the kind and concentration of a component, and the like can be appropriately determined by a person skilled in the art.

The method for measuring ADP is not particularly limited, but the enzymatic measurement method is simple and preferable. Various enzymatic measurement methods of ADP are known, and a reagent for measuring ADP is also commercially available. In the present embodiment, any enzymatic measurement method may be used. For example, a method using pyruvate kinase (PyK) and lactate dehydrogenase (LDH) can be mentioned. In the method, first, as represented by the following formula (2), ADP, phosphoenolpyruvate (PEP), and PyK are contacted to produce pyruvic acid. Then, as represented by the following formula (3), the produced pyruvic acid, nicotinamide adenine dinucleotide reduced form (NADH), and LDH are contacted to produce lactic acid and nicotinamide adenine dinucleotide oxidized form (NAD⁺) (also referred to as NAD).

[Chemical formula 2]

ADP+PEP→pyruvic acid+ATP  (2)

Pyruvic acid+NADH→lactic acid+NAD⁺  (3)

It is known that the absorption spectrum of NADH has an absorption peak near 340 nm, but the absorption spectrum of NAD does not have an absorption peak near 340 nm. As shown in the formulas (2) and (3), NADH decreases with the amount of ADP. Therefore, the change in absorbance near 340 nm due to the decrease in NADH reflects the amount or concentration of ADP in the reaction mixed solution. In the measurement method of ADP using PyK and LDH, ADP is measured based on the absorbance near 340 nm. Since NADH has autofluorescence, ADP may be measured based on the change in fluorescence intensity (excitation wavelength 530 to 570 nm) generated at 590 to 600 nm due to the decrease in NADH.

A method using the PyK and the pyruvate oxidase is also known. In the method, first, as represented by the formula (2), ADP, PEP, and the PyK are contacted to produce pyruvic acid. Then, as represented by the following formula (4), the produced pyruvic acid and the pyruvate oxidase is contacted in the presence of a phosphoric acid (Pi) and oxygen. The enzymatic reaction produces acetyl phosphate, carbon dioxide, and hydrogen peroxide. As shown in the formulas (2) and (4), the amount of hydrogen peroxide produced is proportional to the amount of ADP in the reaction mixed solution. In the measurement method of ADP, ADP is measured by measuring the produced hydrogen peroxide by a color reaction using peroxidase.

[Chemical formula 3]

ADP+PEP→pyruvic acid+ATP  (2)

Pyruvic acid+Pi+O₂→acetyl phosphate+CO₂+H₂O₂  (4)

In the present embodiment, among the enzymatic measurement methods of ADP, a method using ADP dependent hexokinase (ADP-HK) and glucose-6-phosphate dehydrogenase (G6PDH) is preferable. In the method, first, glucose-6-phosphate (G6P) is produced by contacting ADP, glucose, and the ADP-HK as represented by the following formula (5). The reaction is preferably carried out in the presence of the divalent metal ion. Then, as represented by the following formula (6), the produced G6P, NAD⁺, the G6PDH are contacted to produce 6-phosphoglucono-δ-lactone and NADH. As shown in the formulas (5) and (6), the amount of NADH produced is proportional to the amount of ADP in the reaction mixed solution. In the measurement method of ADP, ADP is measured by measuring the produced NADH. In the enzymatic reaction represented by the formula (6), nicotinamide adenine dinucleotide phosphate oxidized form (NADP⁺) (also referred to as NADP) may be used instead of NAD⁺. In the case, the produced nicotinamide adenine dinucleotide phosphate reduced form (NADPH) is measured to measure ADP.

[Chemical formula 4]

ADP+glucose→G6P+AMP  (5)

G6P+NAD⁺→6-phosphoglucono-δ-lactone+NADH  (6)

The measurement of NADH or NADPH can be performed by measuring the absorbance of the reaction mixed solution containing the produced NADH or NADPH. As NADH or NADPH increases, the absorbance of the reaction mixed solution near 340 nm increases. ADP can be measured based on the change in the absorbance. Since NADH and NADPH have autofluorescence, even higher sensitivity can be measured by measuring the fluorescence intensity at 590 to 600 nm generated at an excitation wavelength of 530 to 570 nm. Alternatively, NADH or NADPH may be measured by contacting the produced NADH or NADPH, a coloring reagent, and an electron carrier to produce a dye, and measuring an absorbance of the reaction mixed solution containing the produced dye. The coloring reagent and the electron carrier are commercially available as a reagent for NAD/NADH (or NADP/NADPH) measurement.

The electron carrier is not particularly limited as long as the electron carrier is a substance that can accept an electron from NADH or NADPH and donate an electron to the coloring reagent. Examples of such an electron carrier include diaphorase, phenazine methosulfate, methoxyphenazine methosulfate, and dimethylaminobenzophenoxadinium chloride (Meldola's blue). Among them, diaphorase is particularly preferable.

The coloring reagent is not particularly limited as long as the coloring reagent is a substance that is reduced by donating an electron from the electron carrier to produce a dye. Examples of such a substance include a tetrazolium compound. As shown in the following formula (7), the tetrazolium compound is reduced by the action of the electron carrier to be converted into a formazan dye having various colors. In the reaction represented by the formula (7), NADPH may be used instead of NADH.

[Chemical formula 5]

Tetrazolium compound+NADH→formazan dye+NAD⁺  (7)

The tetrazolium compound is not particularly limited as long as tetrazolium compound is a compound having a tetrazole ring or a salt thereof. As for the tetrazolium compound, various compounds are commercially available as the coloring reagent. For example, WST-1 (2-(4-iodophenyl)-3-(4-nitrophenyl)-5-(2,4-disulfophenyl)-2H-tetrazolium monosodium salt), WST-8 (2-(2-methoxy-4-nitrophenyl)-3-(4-nitrophenyl)-5-(2,4-disulfophenyl)-2H-tetrazolium), NBT (nitroblue tetrazolium), MTT (3-(4,5-dimethyl-2-thiazolyl)-2,5-diphenyl-2H-tetrazolium bromide), and XTT (2,3-bis-(2-methoxy-4-nitro-5-sulfophenyl)-2H-tetrazolium-5-carboxyanilide), INT (2-(4-iodophenyl)-3-(4-nitrophenyl)-5-phenyl-2H-tetrazolium chloride) can be mentioned. Among them, WST-1 or the like that produces a water-soluble formazan dye is preferable.

A biological sample, in particular, a biological sample containing a red blood cell may contain an endogenous adenylate kinase (also called myokinase). Since the adenylate kinase repeatedly reacts with ADP by catalyzing the reaction represented by the formula (8), the method of the present embodiment receives positive interference. To avoid endogenous interference by the adenylate kinase, P1,P5-di(adenosine-5'-) pentaphosphate (Ap5A) which is an inhibitor of the adenylate kinase may be added to the sample or reaction mixed solution. The amount of Ap5A added is represented by the final concentration of Ap5A in the reaction mixed solution at the start of the enzymatic reaction, and is, for example, 1 μM or more and 200 μM or less, further preferably 5 μM or more and 50 μM or less.

[Chemical formula 6]

ATP+AMP→2ADP  (8)

In the present embodiment, it is preferable that the above reaction with the butyrate kinase and the enzymatic measurement method of ADP are carried out in the same reaction system. The reaction system means a limited environment in which a component necessary for an enzymatic reaction is present and the reaction occurs. For example, the reaction with butyrate kinase and the enzymatic measurement method of ADP can be performed in the same reaction system by contacting the sample, ATP, butyrate kinase, and a component used for the enzymatic measurement method of ADP, In such a reaction system, the ADP produced by the enzymatic reaction with the butyrate kinase is immediately consumed by the enzymatic measurement method of ADP. Therefore, the enzymatic reaction represented by the above formula (1) is further promoted toward the production of butyl phosphate and ADP.

Figure 2:
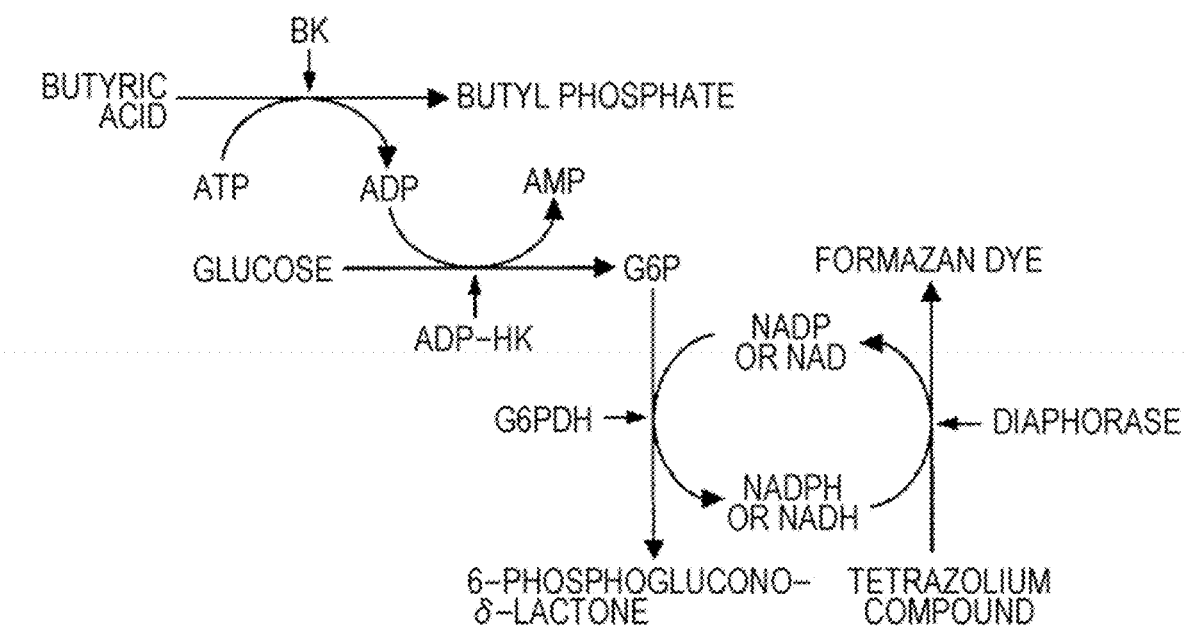
FIG. 2 is a diagram showing a pathway when reactions catalyzed by each of butyrate kinase, ADP-HK, G6PDH, and diaphorase are carried out in the same reaction system.

With reference to FIG. 1, the pathway when the reactions represented by the above formulas (1), (5) and (6) are carried out in the same reaction system is described. The reaction system includes a sample, ATP, butyrate kinase (BK), glucose, NAD or NADP, ADP-HK, and G6PDH. In a preferred embodiment, the reaction system further includes a divalent metal ion. First, butyl phosphate and ADP are produced by contacting the sample, ATP, and the BK. Then, G6P and adenosine monophosphate (AMP) are produced by contacting the produced ADP with glucose and ADP-HK. Then, 6-phosphoglucono-δ-lactone and NADH (or NADPH) are produced by contacting the produced G6P with NAD (or NADP), and G6PDH. In the present embodiment, ADP is measured based on the change in absorbance near 340 nm due to the increase in NADH or NADPH. Alternatively, ADP is measured based on the change in fluorescence intensity (excitation wavelength 530 to 570 nm) generated at 590 to 600 nm due to the increase in NADH or NADPH. FIG. 2 shows a pathway when the reactions represented by the above formulas (1) and (5) to (7) are carried out in the same reaction system. In FIG. 2, a formazan dye and NAD (or NADP) are produced by contacting NADH (or NADPH) produced by the action of G6PDH with a tetrazolium compound and diaphorase. In the present embodiment, ADP is measured based on the change in absorbance due to the increase in the formazan dye.

The measurement of ADP based on the change in absorbance may be performed by a rate assay or an endpoint assay. In the rate assay, ADP in the reaction mixed solution is measured based on the amount of change in absorbance per unit time after the start of the reaction. In the endpoint assay, ADP in the reaction mixed solution is measured based on the difference between the absorbance before reaction start and the absorbance after reaction end.

In the present embodiment, the reaction temperature may be in a temperature range such as room temperature or ordinary temperature at which the enzyme used acts, and is usually 10° C. or higher and 60° C. or lower, preferably 15° C. or higher and 50° C. or lower, and more preferably 20° C. or higher and 40° C. or lower. When using a general-purpose automatic analyzer, 37° C. is preferable. The reaction time is not particularly limited as long as the butyric acid in the sample can be accurately measured, but is 30 seconds or more and 60 minutes or less, preferably 1 minute or more and 30 minutes or less. When using a general-purpose automated analyzer, 10 minutes is especially preferable. The pH of the reaction mixed solution may be in the pH range in which the enzyme used acts, and is usually 6 or more and 10 or less, preferably 6.5 or more and 9.5 or less, and more preferably 7 or more and 8.5 or less. Since the coloring substance using the tetrazolium salt is affected by an endogenous reducing substance at pH 8 or higher, it is better to react at pH 8 or lower. When the reaction with butyrate kinase and the enzymatic measurement method of ADP are carried out in the same reaction system, the reaction temperature, reaction time, and pH can be appropriately selected from the above ranges. The above buffer may be added to the sample or reaction mixed solution to adjust the pH.

In the present embodiment, ADP may be measured after stopping the enzymatic reaction by adding a reaction terminator. The reaction terminator is not particularly limited as long as it is a solution containing a denaturing agent. Examples of the denaturing agent include hydrochloric acid, sulfuric acid, sodium dodecyl sulfate (SDS), and lithium dodecyl sulfate.

[2. Enzymatic Measurement Method of a Short-Chain Fatty Acid Having 3 to 6 Carbon Atoms]

In a further embodiment, an enzymatic measurement method including contacting a short-chain fatty acid having 3 to 6 carbon atoms in a sample, ATP, and butyrate kinase to produce ADP, and measuring the produced ADP is provided. It is known that biological samples obtained from an environment in which a microorganism is present, such as saliva and feces, contains various short-chain fatty acids produced by the microorganism. Examples of the short-chain fatty acid in such a biological sample include acetic acid, propionic acid, and butyric acid, and in general, acetic acid tends to be contained in a larger amount than another fatty acid. On the other hand, in inflammatory diseases such as periodontal disease and Crohn's disease, the action of a short-chain fatty acid other than acetic acid, such as butyric acid and propionic acid produced by an intraoral bacterium or enteric bacterium, attracts attention. Butyrate kinase reacts with a short-chain fatty acid having 3 to 6 carbon atoms containing butyric acid as a substrate, as shown in Reference Example 7 described below. However, butyrate kinase does not react substantially with acetic acid as the substrate. That is, when acetic acid and a short-chain fatty acid having 3 to 6 carbon atoms are mixed in the sample, it is possible to measure a short-chain fatty acid having 3 to 6 carbon atoms without measuring acetic acid by the enzymatic measurement method using butyrate kinase.

Butyrate kinase is an enzyme that catalyzes the reaction represented by the above formula (1), and also catalyzes the same phosphorylation reaction on a short-chain fatty acid having 3 to 6 carbon atoms other than butyric acid. That is, when ATP is contacted with a short-chain fatty acid having 3 to 6 carbon atoms in the presence of butyrate kinase, the phosphate group of ATP is rearranged to the fatty acid to produce phosphorylated fatty acid and ADP. The details of butyrate kinase are as described above.

As used herein, the term "short-chain fatty acid" includes acetic acid, propionic acid, butyric acid, isobutyric acid, valeric acid, isovaleric acid, and caproic acid. Lactic acid and succinic acid are not included in the "short-chain fatty acid" because their properties are quite different (Takashi Sakata, Hirofumi Ichikawa, "Physiological activity of a short-chain fatty acid", Journal of Japan Oil Chemists' Society Vol. 46 (1997) No. 10, PP. 1205-1212). The short-chain fatty acid having 3 to 6 carbon atoms may be linear fatty acid or branched-chain fatty acid. Examples of the short-chain fatty acid having 3 to 6 carbon atoms include propionic acid, butyric acid, isobutyric acid, valeric acid, isovaleric acid, and caproic acid. The short-chain fatty acid having 3 to 6 carbon atoms in the sample may be in a salt or ionic state. Examples of the fatty acid salt include an alkali metal salt and a calcium salt. Examples of the alkali metal salt of the fatty acid include sodium salt, potassium salt, and lithium salt.

The sample is not particularly limited as long as the sample may contain the short-chain fatty acid having 3 to 6 carbon atoms, the salt, or the ion of it. The short-chain fatty acid having 3 to 6 carbon atoms contained in the sample may be one kind or two or more kinds. Examples of such a sample include the above biological sample and the food and drink. As the sample, a culture supernatant of a microorganism that produces a short-chain fatty acid having 3 to 6 carbon atoms may be used. The sample may be diluted with a suitable solvent. The details of the solvent are as described above. In the present embodiment, the sample is preferably liquid. The details of the liquid sample and the preparation are as described above.

The contacting the short-chain fatty acid having 3 to 6 carbon atoms in the sample, ATP, and butyrate kinase to produce ADP can be performed in the same manner as the producing ADP in the method of the present embodiment described above. The final concentrations of butyrate kinase and ATP in the reaction mixed solution are as described above. In the enzymatic measurement method of the present embodiment, the sample, ATP, and butyrate kinase may be contacted in the presence of a divalent metal ion and/or a surfactant. The details of the divalent metal ion, the compound forming the divalent metal ion, and the surfactant are as described above.

In the enzymatic measurement method of the present embodiment, ADP produced by a reaction catalyzed by butyrate kinase is measured. The details of the measurement method of ADP are the same as the description of the method of the present embodiment described above. The amount of ADP produced is proportional to the amount of a short-chain fatty acid having 3 to 6 carbon atoms which is a substrate for butyrate kinase. Therefore, the produced ADP can be measured to measure short-chain fatty acids having 3 to 6 carbon atoms in the sample. That is, the measured value of the produced ADP indicates the total amount of a short-chain fatty acid having 3 to 6 carbon atoms in the sample, or the total amount of a short-chain fatty acid having 3 to 6 carbon atoms per unit volume. The enzymatic measurement method of the present embodiment can be said to be a method for measuring a short-chain fatty acid having 3 to 6 carbon atoms in a sample based on the measurement result of ADP produced by contacting the sample, ATP, and butyrate kinase.

In the present embodiment, the value of the total amount of a short-chain fatty acid having 3 to 6 carbon atoms in the sample or the total amount of a short-chain fatty acid having 3 to 6 carbon atoms per unit volume may be determined from the measured value of ADP using a calibration curve. On the other hand, since it is often unclear which short-chain fatty acid is specifically contained in the sample, it is difficult to strictly prepare a standard solution for creating a calibration curve. Therefore, a standard solution for creating a calibration curve may be prepared on the assumption that there is one kind of a short-chain fatty acid having 3 to 6 carbon atoms in the sample. For example, an aqueous solution containing any one kind selected from a short-chain fatty acid having 3 to 6 carbon atoms at a predetermined concentration is prepared. Which of the short-chain fatty acid having 3 to 6 carbon atoms is selected is not particularly limited, and for example, the short-chain fatty acid considered to be contained most in the sample to be measured may be selected. In a preferred embodiment, a butyric acid aqueous solution having a known concentration is used as a standard solution for creating a calibration curve. The standard solution in the same manner as the sample can be measured to create a calibration curve showing the relation between the measured value of ADP and the concentration of a short-chain fatty acid.

[3. Reagent for Enzymatic Measurement]

The reagent for enzymatic measurement of the present embodiment (hereinafter, also simply referred to as "reagent") includes butyrate kinase and ATP. The reagent of the present embodiment is used in the above enzymatic measurement method of the present embodiment. The reagent of the present embodiment may be in the form of one reagent containing both butyrate kinase and ATP in one reagent. Alternatively, the reagent of the present embodiment may be in the form of two reagents including a first reagent containing ATP and a second reagent containing butyrate kinase.

Figure 3:
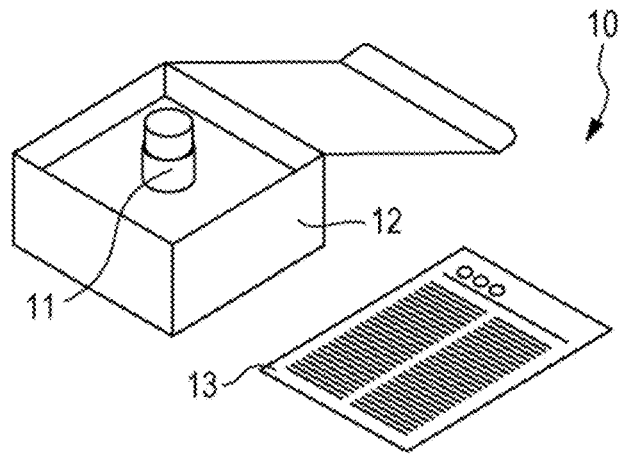
FIG. 3 is a schematic diagram showing an example of a reagent in the form of one reagent.
Figure 4:
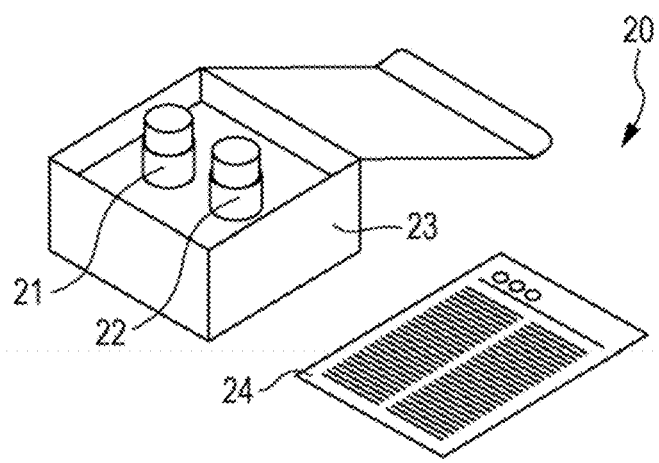
FIG. 4 is a schematic diagram showing an example of reagents in the form of two reagents.

In the present embodiment, the container containing the reagent may be packed in a box and provided to the user. The box may include a package leaflet that describes how to use the reagent. FIGS. 3 and 4 show examples of the reagents of the present embodiment. With reference to FIG. 3, 10 indicates a reagent in the form of one reagent, 11 indicates a first container containing the reagent, 12 indicates a packing box, and 13 indicates a package leaflet. With reference to FIG. 4, 20 indicates a reagent in the form of two reagents, 21 indicates a first container containing a first reagent, 22 indicates a second container containing a second reagent, and 23 indicates a packing box and 24 indicates a package leaflet.

The reagent of the present embodiment may contain butyrate kinase and ATP in a solid state (powder, crystal, lyophilized product, etc.). Alternatively, the reagent of the present embodiment may be contained in the form of a solution in which butyrate kinase and ATP are dissolved in a suitable solvent. When the reagents are in the form of two reagents, either one of the first reagent and the second reagent may be in the solid state, and the other one may be in the solution state. Preferably, both the first reagent and second reagent are in the solution state. Examples of the solvent include aqueous solvents such as water, physiological saline, and a buffer. The details of the buffer are as described above.

When the reagent is in the solution state, the concentration of butyrate kinase in the reagent may be the concentration at which the final concentration of butyrate kinase when the reagent and the sample are mixed can be within the above numerical range. Therefore, the concentration of butyrate kinase in the reagent can be determined from the mixing ratio of the reagent and the sample. In the present embodiment, the lower limit of the concentration of butyrate kinase in the reagent is, for example, 0.02 U/mL or more, preferably 0.2 U/mL or more, and further preferably 1 U/mL or more, and the upper limit of the concentration is, for example, 750 U/mL or less, preferably 250 U/mL or less, and further preferably 100 U/mL or less.

When the reagent is in the solution state, the concentration of ATP in the reagent may be a concentration that allows the final concentration of ATP when the reagent and the sample are mixed within the above numerical range. Therefore, the concentration of ATP in the reagent can be determined from the mixing ratio of the reagent and the sample. In the present embodiment, the lower limit of the concentration of ATP in the reagent is, for example, 0.2 mM or more, preferably 0.4 mM or more, and further preferably 1 mM or more, and the upper limit of the concentration is, for example, 250 mM or less, preferably 50 mM or less, and further preferably 25 mM or less.

When the reagent is in the solution state, the pH of the reagent is usually 6 or more and 10 or less, preferably 6.5 or more and 9.5 or less, and more preferably 7 or more and 8.5 or less. Even when the reagent is in the form of two reagents, the pH can be appropriately determined from the above range. The above buffer may be added to the reagent to adjust the pH. The optimum pH of butyrate kinase is 8 to 9, but pH 7 to 7.5 is also sufficiently active. Therefore, when another component contained in the reagent together with butyrate kinase is stable at a pH near neutral, the pH of the reagent may be adjusted to 7 to 7.5. Examples of another component include a component used in the enzymatic measurement method of ADP, the coloring reagent, and the electron carrier. In particular, when the reagent contains the tetrazolium compound, the pH of the reagent is preferably 7.5 or less.

The reagent of the present embodiment preferably further includes a divalent metal ion. A compound that forms a divalent metal ion is added to the reagent, and thus the reagent can contain a divalent metal ion. Details of the compounds that form divalent metal ions are as described above. Examples of the divalent metal ion include magnesium ion and zinc ion. Among them, the magnesium ion is particularly preferable. The concentration of the divalent metal ion in the reagent may be any concentration as long as the final concentration of the divalent metal ion when the reagent and the sample are mixed can be within the above numerical range. Therefore, the concentration of the divalent metal ion in the reagent can be determined from the mixing ratio of the reagent and the sample. In the present embodiment, the lower limit of the concentration of the divalent metal ion in the reagent is, for example, 0.2 mM or more, preferably 1 mM or more, and further preferably 2 mM or more, and the upper limit of the concentration is, for example, 250 mM or less, preferably 100 mM or less, and further preferably 50 mM or less.

The reagent of the present embodiment may further contain the component used in the enzymatic measurement method of ADP. Examples of the component used in the enzymatic measurement method of ADP include an enzyme, a substrate, and a coenzyme. In a preferred embodiment, the reagent further includes glucose, ADP-HK, NAD or NADP, and G6PDH. When the reagents are in the form of two reagents, the above component may be contained in either the first reagent or the second reagent, respectively. The concentration of each component in the reagent is not particularly limited as long as ADP in the reaction mixed solution can be accurately measured. Such a concentration can be appropriately determined by a person skilled in the art by referring to, for example, a commercially available reagent for measuring ADP. As an example of the concentration of each component in the reagent, the concentration of glucose is 0.1 mM or more and 100 mM or less, the concentration of ADP-HK is 0.2 U/mL or more and 20 U/mL or less, and the concentration of NAD or NADP is 0.1 mM or more and 5 mM or less, and the concentration of G6PDH is 0.2 U/mL or more and 20 U/mL or less.

When the reagent contains glucose, ADP-HK, NAD or NADP, and G6PDH, the reagent may further contain a coloring reagent and an electron carrier. When the reagent is in the form of two reagents, the coloring reagent and the electron carrier may be contained in either the first reagent or the second reagent, respectively. The details of the coloring reagent and the electron carrier are as described above. Each concentration of the coloring reagent and the electron carrier in the reagent is not particularly limited as long as ADP in the reaction mixed solution can be accurately measured. Such a concentration can be appropriately determined by a person skilled in the art by referring to, for example, a commercially available reagent for measuring NAD/NADH (or NADP/NADPH). When the tetrazolium compound is contained as the coloring reagent, the concentration in the reagent is, for example, 0.05 mM or more and 5 mM or less. When diaphorase is contained as the electron carrier, the concentration in the reagent is, for example, 0.1 U/mL or more and 10 U/mL or less.

If necessary, the reagent may further contain a surfactant. The reagent may further contain an inorganic salt. When the reagents are in the form of two reagents, the surfactant and the inorganic salt may be contained in either the first reagent or the second reagent, respectively. The details of the surfactant and the inorganic salt are as described above. When the reagent contains a nonionic surfactant, the concentration in the reagent is, for example, 0.01% (W/V) or more and 2% (W/V) or less. When the reagent contains a potassium salt, the concentration in the reagent is, for example, 1 mM or more and 200 mM or less.

The reagent of the present embodiment may be provided as a reagent kit together with the reaction terminator solution contained in the container. The details of the reaction terminator are as described above. The concentration of the denaturing agent in the reaction terminator can be appropriately determined depending on the kind of the denaturing agent. When SDS or lithium dodecyl sulfate is contained as the denaturing agent, the concentration in the reaction terminator is, for example, 0.1% (W/V) or more and 10% (W/V) or less.

The reagent of the present embodiment may be a reagent for diagnosing periodontal disease. The present embodiment relates to a method for assisting a diagnosis of periodontal disease, the method including measuring a short-chain fatty acid having 3 to 6 carbon atoms in a sample derived from a subject using the reagent. Another embodiment relates to the use of butyrate kinase and ATP for the production of a reagent for enzymatic measurement. A further embodiment relates to the use of butyrate kinase and ATP for the production of a reagent for diagnosing periodontal disease Hereinafter, the present disclosure is described in detail with reference to Examples, but the present disclosure is not limited to these Examples.

EXAMPLES

In Reference Examples 1 to 6, a gene encoding butyrate kinase was cloned from chromosomal DNA of various microorganisms, and recombinant butyrate kinase was obtained using an *Escherichia coli* expression system.

Reference Example 1: Preparation of Butyrate Kinase Derived from *Acetoanaerobium sticklandii*

(1) Preparation of Transformant

Using the chromosomal DNA of *Acetoanaerobium sticklandii* (DSM No. 519) purchased from Leibniz Institute DSMZ as a template, PCR was performed using a sense primer (SEQ ID NO: 1), an antisense primer (SEQ ID NO: 2), and KOD FX (product number: KFX-101, TOYOBO CO., LTD.), and the butyrate kinase gene was amplified to obtain a PCR product of about 1100 bp. The base sequence of the obtained PCR product was confirmed by sequencing. The base sequence of butyrate kinase derived from *Acetoa-* naerobium sticklandii and the amino acid sequence deduced from the base sequence are shown in SEQ ID NOs: 16 and 17, respectively. The obtained PCR product was digested with EcoRI (Takara Bio Inc.) and HindIII (Takara Bio Inc.), and inserted into the EcoRI-HindIII site of pET-21a(+) vector (Novagen) which is the expression vector to obtain an astBK/pET21a(+) expression plasmid. In the expression plasmid, a vector-derived T7 tag and a base sequence encoding a linker were added to the 5' end of the butyrate kinase gene. A base sequence encoding a vector-derived linker and His tag were added to the 3' end of the butyrate kinase gene. That is, the astBK/pET21a(+) expression plasmid contained a polynucleotide encoding a T7 tag-linker-butyrate kinase-linker-His tag. The expression plasmid was introduced into One shot BL21(DE3) Chemically Competent *E. coli* (Invitrogen) to obtain a transformant astBK/pET-21a(+)/BL21(DE3) having a recombinant vector containing a polynucleotide encoding a butyrate kinase derived from *Acetoanaerobium sticklandii*.

(2) Preparation of Recombinant Butyrate Kinase (2.1) Induction of Butyrate Kinase in Transformant and Preparation of Crude Enzyme Solution One colony of the above transformant was taken, inoculated into a 50 µg/mL ampicillin-containing LB liquid medium (5 mL), and cultured in a test tube at about 25° C. for about 16 hours. The culture (1.6 mL) was added to 50 µg/mL ampicillin-containing liquid medium (1.6 L) (1% glycerol-containing Overnight Express (trademark) Instant TB Medium (Merck & Co., Inc.), 0.1% ADEKA NOL LG-109 (ADEKA Corporation)), and cultured in a jar fermenter at 30° C., pH 6.8, and 650 rpm for about 25 hours. The culture was centrifuged to collect a cell, and the obtained bacterial cell was suspended in a solution A (10 mM potassium phosphate buffer (pH 7.5), 0.3 M NaCl). The bacterial cell in the suspension was crushed by an ultrasonic wave to be solubilized, and then centrifuged to obtain a supernatant. The supernatant was used as a crude enzyme solution.

(2.2) Purification of Recombinant Butyrate Kinase

Chelating Sepharose Fast Flow (GE Healthcare) was packed in a column to immobilize $Ni^{2+}$ and then equilibrated with the solution A. The above crude enzyme solution was added to the obtained column to adsorb recombinant butyrate kinase. After washing the column with the solution A, recombinant butyrate kinase was eluted with a linear gradient of 10 CV (column volume) using the solution A and a solution A containing 0.4 M imidazole. The active fraction of the obtained recombinant butyrate kinase was concentrated in a pencil-type module (UF) (Asahi Kasei Chemicals Corporation) to 1/10 volume, and desalted on a PD-10 column (GE Healthcare) equilibrated with 10 mM potassium phosphate buffer (pH 7.5) to obtain a solution of the recombinant butyrate kinase. A part of the obtained butyrate kinase solution was taken and analyzed by SDS-PAGE. The results are shown in FIG. 5. In the drawing, lane 1 indicates an enzyme solution, lane 2 indicates a molecular weight marker, and an arrow indicates a band corresponding to butyrate kinase. Hereinafter, the recombinant butyrate kinase derived from *Acetoanaerobium sticklandii* obtained in Reference Example 1 is also referred to as "BKII".

Reference Example 2: Preparation of Butyrate Kinase Derived from *Thermosediminibacter oceani* (1)

Using the chromosomal DNA of *Thermosediminibacter oceani* (DSM No. 16646) purchased from Leibniz Institute DSMZ as a template, PCR was performed using a sense primer (SEQ ID NO: 3), an antisense primer (SEQ ID NO: 4), and KOD FX (product number: KFX-101), and the butyrate kinase gene was amplified to obtain a PCR product of about 1100 bp. The base sequence of the obtained PCR product was confirmed by sequencing. The base sequence of butyrate kinase derived from *Thermosediminibacter oceani* in Reference Example 2 and the amino acid sequence deduced from the base sequence are shown in SEQ ID NOs: 18 and 19, respectively. The obtained PCR product was digested with NdeI (Takara Bio Inc.) and HindIII and inserted into the NdeI-HindIII site of the pET-21a(+) vector to obtain a ToBK/pET21a(+) expression plasmid. In the expression plasmid, a vector-derived linker and a base sequence encoding His tag were added to the 3' end of the butyrate kinase gene. That is, the ToBK/pET21a(+) expression plasmid contained a polynucleotide encoding a butyrate kinase-linker-His tag. The expression plasmid was introduced into One shot BL21(DE3) Chemically Competent *E. coli* (Invitrogen) to obtain a transformant ToBK/pET-21a (+)/BL21(DE3) having a recombinant vector containing a polynucleotide encoding a butyrate kinase derived from *Thermosediminibacter oceani*. The obtained transformant was cultured in the same manner as in Reference Example 1, and a crude enzyme solution was prepared from the bacterial cell. The obtained crude enzyme solution was purified in the same manner as in Reference Example 1 to obtain a solution of recombinant butyrate kinase. A part of the obtained butyrate kinase solution was taken and analyzed by SDS-PAGE. The results are shown in FIG. 6. In the drawing, lane 1 indicates an enzyme solution, lane 2 indicates a molecular weight marker, and an arrow indicates a band corresponding to butyrate kinase.

Reference Example 3: Preparation of Butyrate Kinase Derived from *Thermosediminibacter oceani* (2)

Using the chromosomal DNA of *Thermosediminibacter oceani* (DSM No. 16646) purchased from Leibniz Institute DSMZ as a template, PCR was performed using a sense primer (SEQ ID NO: 3), an antisense primer (SEQ ID NO: 5), and KOD FX (product number: KFX-101), and the butyrate kinase gene was amplified to obtain a PCR product of about 1100 bp. The base sequence of the obtained PCR product was confirmed by sequencing. The base sequence of the butyrate kinase and the amino acid sequence deduced from the base sequence were the same as the sequences represented by SEQ ID NOs: 18 and 19, respectively. The obtained PCR product was digested with NdeI and HindIII and inserted into the NdeI-HindIII site of the pET-21a(+) vector to obtain a ToBKIII/pET21a(+) expression plasmid. In the expression plasmid, the tag was not added to the butyrate kinase gene. The expression plasmid was introduced into One shot BL21(DE3) Chemically Competent *E. coli* (Invitrogen) to obtain a transformant ToBKIII/pET-21a (+)/BL21(DE3) having a recombinant vector containing a polynucleotide encoding a butyrate kinase derived from *Thermosediminibacter oceani*. The obtained transformant was cultured in the same manner as in Reference Example 1. The culture was centrifuged to collect a cell, and the obtained bacterial cell was suspended in 20 mM Tris-HCl (pH 7.5). The bacterial cell in the suspension was crushed by an ultrasonic wave to be solubilized, and then centrifuged to obtain a supernatant. The supernatant was used as a crude enzyme solution.

Q Sepharose Fast Flow (GE Healthcare) was packed in a column and equilibrated with 10 mM Tris-HCl (pH 8.0) solution. The above crude enzyme solution was added to the obtained column to adsorb recombinant butyrate kinase. The recombinant butyrate kinase was then eluted with a 10 CV (column volume) linear gradient using a 10 mM Tris-HCl (pH 8.0) solution and a 10 mM Tris-HCl (pH 8.0) solution containing 0.5 M KCl. The active fraction of the recombinant butyrate kinase was confirmed, and ammonium sulfate was added so as to be 18%. Phenyl Sepharose 6 Fast Flow (high sub) (GE Healthcare) was packed in a column and equilibrated with a 10 mM Tris-HCl (pH 8.0) solution containing 18% ammonium sulfate, and the above active fraction containing 18% ammonium sulfate was adsorbed. The recombinant butyrate kinase was then eluted with a 10 CV linear gradient using a 10 mM Tris-HCl (pH 8.0) solution containing 18% ammonium sulfate and a 10 mM Tris-HCl (pH 8.0) solution. The active fraction of the recombinant butyrate kinase was confirmed and recovered. The active fraction of the obtained recombinant butyrate kinase was concentrated in an Amicon Ultra-15 centrifugal filter unit (Millipore Corporation), and buffer exchanged in a PD-10 column (GE Healthcare) with a 10 mM Tris-HCl (pH 8.0) solution to obtain a solution of recombinant butyrate kinase. A part of the obtained butyrate kinase was analyzed by SDS-PAGE. The results are shown in FIG. 7. In the drawing, lane 1 indicates an enzyme solution, lane 2 indicates a molecular weight marker, and an arrow indicates a band corresponding to butyrate kinase. Hereinafter, the recombinant butyrate kinase derived from *Thermosediminibacter oceani* obtained in Reference Example 3 is also referred to as "BKIII".

Reference Example 4: Preparation of Butyrate Kinase Derived from *Thermosediminibacter oceani* (3)

Using the chromosomal DNA of *Thermosediminibacter oceani* (DSM No. 16646) purchased from Leibniz Institute DSMZ as a template, PCR was performed using a sense primer (SEQ ID NO: 6), an antisense primer (SEQ ID NO: 7), and KOD FX (product number: KFX-101), and the butyrate kinase gene was amplified to obtain a PCR product of about 1100 bp. The base sequence of the obtained PCR product was confirmed by sequencing. The base sequence of butyrate kinase derived from *Thermosediminibacter oceani* in Reference Example 4 and the amino acid sequence deduced from the base sequence are shown in SEQ ID NOs: 20 and 21, respectively. The obtained PCR product was digested with NdeI and HindIII and inserted into the NdeI-HindIII site of the pET-21a(+) vector to obtain a ToBK2/pET21a(+) expression plasmid. In the expression plasmid, a vector-derived linker and a base sequence encoding His tag were added to the 3' end of the butyrate kinase gene. That is, the ToBK2/pET21a(+) expression plasmid contained a polynucleotide encoding a butyrate kinase-linker-His tag. Using the ToBK2/pET21a(+) expression plasmid, a solution of recombinant butyrate kinase derived from *Thermosediminibacter oceani* was obtained in the same manner as in Reference Example 2.

Reference Example 5: Preparation of Butyrate Kinase Derived from *Natranaerobius thermophilus*

Using the chromosomal DNA of *Natranaerobius thermophilus* (DSM No. 18059) purchased from Leibniz Institute DSMZ as a template, PCR was performed using a sense primer (SEQ ID NO: 8), an antisense primer (SEQ ID NO: 9), and KOD FX (product number: KFX-101), and the butyrate kinase gene was amplified to obtain a PCR product of about 1100 bp. The base sequence of the obtained PCR product was confirmed by sequencing. The base sequence of butyrate kinase derived from *Natranaerobius thermophilus* and the amino acid sequence deduced from the base sequence are shown in SEQ ID NOs: 22 and 23, respectively. The obtained PCR product was digested with NdeI and HindIII and inserted into the NdeI-HindIII site of the pET-21a(+) vector to obtain a NtBK/pET21a(+) expression plasmid. In the expression plasmid, a vector-derived linker and a base sequence encoding His tag were added to the 3' end of the butyrate kinase gene. That is, the NtBK/pET21a(+) expression plasmid contained a polynucleotide encoding a butyrate kinase-linker-His tag. Using the NtBK/pET21a(+) expression plasmid, a solution of recombinant butyrate kinase derived from *Natranaerobius thermophilus* was obtained in the same manner as in Reference Example 2.

Reference Example 6: Preparation of Butyrate Kinase Derived from *Symbiobacterium thermophilum*

Using the chromosomal DNA of *Symbiobacterium thermophilum* (DSM No. 24528) purchased from Leibniz Institute DSMZ as a template, PCR was performed using a sense primer (SEQ ID NO: 10), an antisense primer (SEQ ID NO: 11), and KOD FX (product number: KFX-101), and the butyrate kinase gene was amplified to obtain a PCR product of about 1100 bp. The base sequence of the obtained PCR product was confirmed by sequencing. The base sequence of butyrate kinase derived from *Symbiobacterium thermophilum* and the amino acid sequence deduced from the base sequence are shown in SEQ ID NOs: 24 and 25, respectively. The obtained PCR product was digested with NdeI and HindIII, and inserted into the NdeI-HindIII site of the pET-21a(+) vector to obtain a StBK/pET21a(+) expression plasmid. In the expression plasmid, a vector-derived linker and a base sequence encoding His tag were added to the 3' end of the butyrate kinase gene. That is, the StBK/pET21a(+) expression plasmid contained a polynucleotide encoding a butyrate kinase-linker-His tag. Using the StBK/pET21a(+) expression plasmid, a solution of recombinant butyrate kinase derived from *Symbiobacterium thermophilum* was obtained in the same manner as in Reference Example 2.

Example 1: Measurement of Recombinant Butyrate Kinase Activity

The enzymatic activity of BKII and BKIII with respect to butyric acid was measured based on the amount of ADP produced. In the Example 1, ADP produced by the action of butyrate kinase is used to produce NADPH by the action of ADP dependent hexokinase and glucose-6-phosphate dehydrogenase (see FIG. 1), and the amount of ADP produced was measured based on the change in absorbance at 340 nm due to the increase in NADPH. The measurement was performed using a 7080 type Hitachi automatic analyzer (Hitachi High-Tech Corporation).
  (1) Reagent and Equipment
  [Composition of First Reagent]
  50 mM Tris-HCl (pH 7.5) (Sigma-Aldrich Co. LLC.)
  2 mM ATP (pH 7.5) (Oriental Yeast Co., Ltd.)
  2 mM $MgCl_2$ (FUJIFILM Wako Pure Chemical Corporation)
  20 mM glucose (FUJIFILM Wako Pure Chemical Corporation)

100 mM sodium butyrate (FUJIFILM Wako Pure Chemical Corporation)
1 mM NADP (FUJIFILM Wako Pure Chemical Corporation)
5 U/mL G6PDH II (Glucose-6-phosphate dehydrogenase: T-51, ASAHI KASEI PHARMA CORPORATION)
5 U/mL ADP-HK II (ADP dependent hexokinase: T-92, ASAHI KASEI PHARMA CORPORATION)
0.1% TN-100 (ADEKA Corporation)
[Composition of BKII Diluent]
50 mM Tris-HCl (pH 7.5) (Sigma-Aldrich Co. LLC.)
10 mM KCl (FUJIFILM Wako Pure Chemical Corporation)
[Composition of BKIII Diluent]
50 mM Potassium phosphate buffer (pH 7.0) (Sigma-Aldrich Co. LLC.)
0.1% TN-100 (ADEKA Corporation)
[Measurement Parameters of Automatic Analyzer]
Analysis method: Rate-A
Measurement wavelength (secondary/primary): 700 nm/340 nm
Reaction time: 5 minutes
Photometry point: 11 to 16
Sample volume: 3 μL
First reagent amount: 150 μL (2) Preparation of Sample The BKII solution obtained in Reference Example 1 was diluted 200-fold with a BKII diluent to prepare a sample containing BKII. The BKIII solution obtained in Reference Example 3 was diluted 40,000-fold with a BKIII diluent to prepare a sample containing BKIII.

(3) Measurement of Enzymatic Activity

The sample was dispensed into a cuvette, then the first reagent was added and stirred. The mixed solution of the sample and the first reagent was incubated at 37° C. for 5 minutes. The cuvette was irradiated with light and the change in absorption at 340 nm was measured between about 200 seconds and about 296 seconds after the addition of the first reagent. These operations were performed by the automatic analyzer. The activity value (U/mL) of butyrate kinase was calculated from the following formula by defining the amount of enzyme that phosphorylates 1 μmol of butyric acid per minute as 1 U and using the value of the absorbance change per minute (ΔmAbs/min) calculated from the absorbance at the photometry point and the millimole extinction coefficient (ε=6.3) of NADH at 340 nm. As a result, the activity value of BKII was about 340 U/mL, and the activity value of BKIII was about 1800 U/mL.

Activity value of butyrate kinase (U/mL)=

[(AmAbs/min)/(activity value coefficient of millimole molecular extinction coefficient at 340 nm of NADH)]×[(sample volume+first reagent amount)/(sample volume)]×(dilution of enzyme)=

[(ΔmAbs/min)/6.3]×[(3+150)/3]×(dilution of enzyme)

Reference Example 7: Measurement of Various Parameters of Recombinant Butyrate Kinase (1) Specific Activity The specific activity (U/mg) is the activity value per 1 mg of enzyme. The protein (enzyme) concentrations of the BKII solution obtained in Reference Example 1 and the BKIII solution obtained in Reference Example 3 were quantified by the Bradford method, and the specific activities of BKII and BKIII with respect to butyric acid under the measurement conditions of Example 1 were calculated. As a result, the specific activity of BKII was about 337 U/mg, and the specific activity of BKIII was about 513 U/mg.

(2) Michaelis-Menten Constant and Maximum Velocity

The Km and Vmax of BKII and BKIII with respect to butyric acid under the measurement conditions of Example 1 were determined by Lineweaver-Burk plot. As a result, the Km of BKII was 4.2 mM, and the Km of BKIII was 1.9 mM. The Vmax of BKII was 1100 U/mg and the Vmax of BKIII was 450 U/mg.

(3) Substrate Specificity

The substrate specificity of BKII and BKIII was examined using the following first reagent and second reagent. Various fatty acids shown in Table 1 were used as a substrate. The measurement was performed using a 7180 type Hitachi automatic analyzer (Hitachi High-Tech Corporation).

(3.1) Reagents, Sample, and Equipment
[Composition of First Reagent]
100 mM Tris-HCl (pH 7.5) (Sigma-Aldrich Co. LLC.)
2 mM ATP (pH 7.5) (Oriental Yeast Co., Ltd.)
2 mM MgCl$_2$ (FUJIFILM Wako Pure Chemical Corporation)
20 mM glucose (FUJIFILM Wako Pure Chemical Corporation)
1 mM NADP (FUJIFILM Wako Pure Chemical Corporation)
5 U/mL G6PDH II (Glucose-6-phosphate dehydrogenase: T-51, ASAHI KASEI PHARMA CORPORATION)
5 U/mL ADP-HK II (ADP dependent hexokinase: T-92, ASAHI KASEI PHARMA CORPORATION)
[Composition of Second Reagent]
Substrate
100 mM Tris-HCl (pH 7.5)
100 mM sodium salts of various fatty acids In the composition of the second reagent, "sodium salts of various fatty acids" means any one kind of sodium caprylate, sodium caproate, sodium valerate, sodium isovalerate, sodium butyrate, sodium isobutyrate, sodium propionate, sodium acetate, sodium lactate, and sodium succinate. Isobutyric acid, valeric acid, isovaleric acid, caproic acid, and octanoic acid, which are commercially available fatty acids and are not sold as sodium salts, were adjusted to pH 7.5 with sodium hydroxide.
[Composition of Sample]
1 U/mL BKH (dissolved in BKII diluent) or BKHI (dissolved in BKIII diluent)
[Measurement Parameters of Automatic Analyzer]
Analysis method: Rate-A
Measurement wavelength (secondary/primary): 700 nm/340 nm
Reaction time: 10 minutes
Photometry point: 20 to 23
Sample volume: 3.5 μL
First reagent amount: 140 μL
Second reagent amount: 35 μL (3.2) Results The results are shown in Table 1. In the table, the substrate specificity is shown as a relative value (%) when the activity value with respect to butyric acid is 100. As shown in Table 1, butyrate kinase reacted little with octanoic acid, acetic acid, lactic acid, and succinic acid, but reacted with caproic acid, valeric acid, isovaleric acid, butyric acid, isobutyric acid, and propionic acid. It was found that butyrate kinase uses a short-chain fatty acid having 3 to 6 carbon atoms as a substrate.

TABLE 1

| Substrate | BKII | BKIII |
|---|---|---|
| Octanoic acid | 0 | 0 |
| Caproic acid | 22 | 56 |
| Valeric acid | 161 | 138 |
| Isovaleric acid | 133 | 148 |
| Butyric acid | 100 | 100 |
| Isobutyric acid | 84 | 80 |
| Propionic acid | 62 | 41 |
| Acetic acid | 1 | 1 |
| Lactic acid | 0 | 0 |
| Succinic acid | 2 | 0 |

(4) Isoelectric Point

As a result of calculating the isoelectric points of BKII and BKIII using GENETYX Ver. 10 (GENETYX CORPORATION), the isoelectric point of BKII was 6.31 and the isoelectric point of BKIII was 4.99.

(5) Optimum pH

Figure 8:
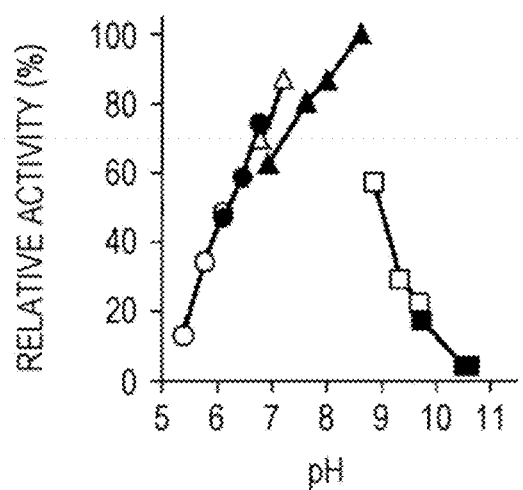
FIG. 8 is a graph showing the optimum pH of the recombinant butyrate kinase derived from *Acetoanaerobium sticklandii*.
Figure 9:
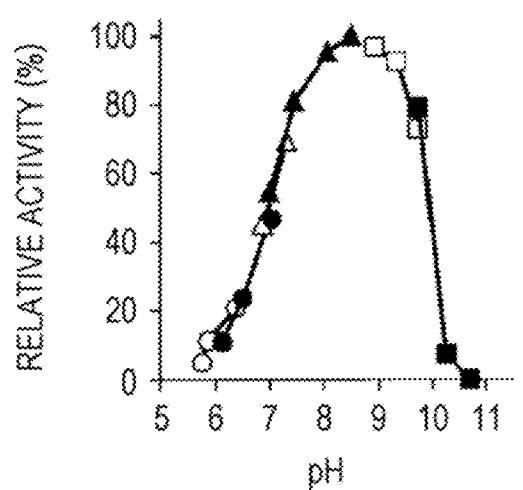
FIG. 9 is a graph showing the optimum pH of the recombinant butyrate kinase derived from *Thermosediminibacter oceani*.

The activity values of BKII and BKIII were measured in the same manner except that the Tris-HCl (pH 7.5) buffer in the first reagent used in Example 1 was replaced with the following buffers. The buffers used were Acetate-NaOH (pH 5 to 6), MES-NaOH (pH 6 to 7), PIPES-NaOH (pH 7 to 7.5), Tris-HCl (pH 7 to 9), CHES-NaOH (pH 9 to 10), and CAPS-NaOH (pH 10 to 11). The measurement results are shown in FIGS. 8 and 9. In the drawing, the activity value is shown as a relative value. From FIGS. 8 and 9, the optimum pH of BKII was 8 to 9, and the optimum pH of BKIII was 8 to 9.3.

(6) Molecular Weight

The molecular weights of BKII and BKIII were determined by SDS-PAGE method. As a result, the molecular weight of BKII was about 41,000, and the molecular weight of BKIII was about 39,000. When the molecular weights of BKII and BKIII were calculated from their respective amino acid sequences, the molecular weight of BKII was about 42,339, and the molecular weight of BKIII was about 39,088.

(7) pH Stability

Figure 10:
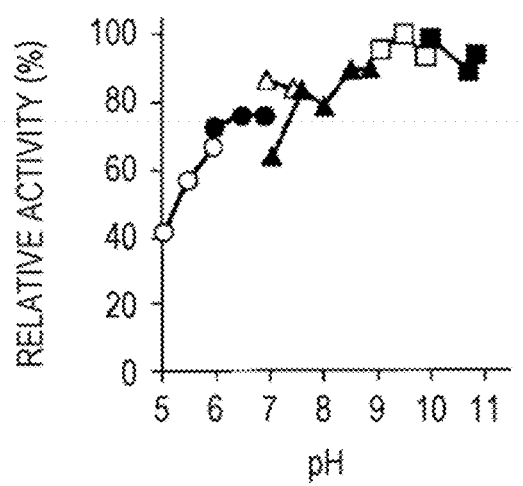
FIG. 10 is a graph showing the pH stability of the recombinant butyrate kinase derived from *Acetoanaerobium sticklandii*.
Figure 11:
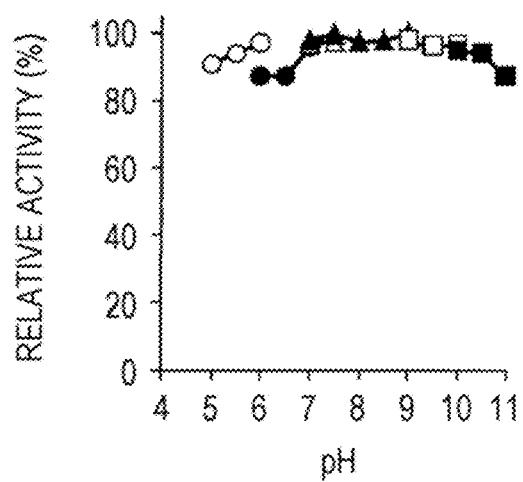
FIG. 11 is a graph showing the pH stability of the recombinant butyrate kinase derived from *Thermosediminibacter oceani*.

The pH stability of BKII was examined based on the remaining activity after incubating approximately 2.4 µg/mL BKII at 37° C. for 30 minutes in the following 10 mM buffer containing 100 mM KCl. The pH stability of BKIII was examined based on the remaining activity after incubating approximately 1 U/mL BKIII at 37° C. for 5 hours in the following 50 mM buffer containing 0.1% TN-100. The remaining activity was measured in the same manner as in Example 1. The buffers used were Acetate-NaOH (pH 5 to 6), MES-NaOH (pH 6 to 7), PIPES-NaOH (pH 7 to 7.5), Tris-HCl (pH 7 to 9), CHES-NaOH (pH 9 to 10), and CAPS-NaOH (pH 10 to 11). The measurement results are shown in FIGS. 10 and 11. From FIGS. 10 and 11, the pH stability of BKII was in the range of pH 8 to 11 (for 30 minutes at 37° C.), and the pH stability of BKIII was in the range of pH 5 to 11 (for 5 hours at 37° C.).

(8) Thermal Stability

Figure 12:
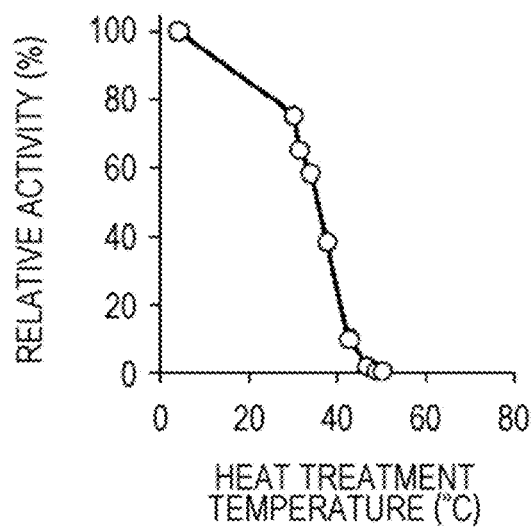
FIG. 12 is a graph showing the thermal stability of the recombinant butyrate kinase derived from *Acetoanaerobium sticklandii*.
Figure 13:
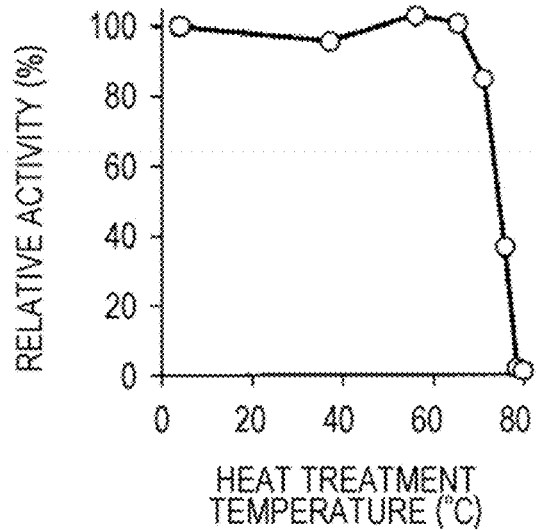
FIG. 13 is a graph showing the thermal stability of the recombinant butyrate kinase derived from *Thermosediminibacter Oceani*.

The thermal stability of BKII was examined based on the remaining activity after incubating approximately 0.3 mg/mL BKII at each temperature of 4 to 50° C. for 30 minutes in 10 mM Tris-HCl buffer (pH 7.5) containing 100 mM KCl. The thermal stability of BKIII was examined based on the remaining activity after incubating approximately 1 mg/mL BKIII in 50 mM potassium phosphate buffer (pH 7) containing 0.1% TN-100 (ADEKA Corporation) at each temperature of 4 to 80° C. for 30 minutes. The remaining activity was measured in the same manner as in Example 1. The measurement results are shown in FIGS. 12 and 13. From FIGS. 12 and 13, the thermal stability (remaining activity) of BKII was 50% or more after treatment at 37° C. for 30 minutes, and the thermal stability (remaining activity) of BKIII was 85% or more after treatment at 70° C. for 30 minutes.

The thermal stability of BKIII, Thermosediminibacter oceani-derived butyrate kinase (ToBK2) prepared in Reference Example 4, Natranaerobius thermophilus-derived butyrate kinase (NtBK) prepared in Reference Example 5, and Symbiobacterium thermophilum-derived butyrate kinase (StBK) prepared in Reference Example 6 were compared. Specifically, each butyrate kinase was added to a 50 mM potassium phosphate buffer (pH 7) containing 0.1% TN-100 so that the concentration is about 1 mg/mL, and the remaining activity after incubating at 65° C. for 30 minutes was measured. The remaining activity was measured in the same manner as in Example 1. The remaining activities of BKIII, ToBK2, NtBK, and StBK were 81.6%, 60.5%, 14.7%, and 48.7%, respectively.

Example 2: Linearity Test

In order to confirm the accuracy of the quantification of butyric acid measurement using butyrate kinase, the linearity of the calibration curve was confirmed. The measurement was performed using a 7180 type Hitachi automatic analyzer (Hitachi High-Tech Corporation).

(1) Samples, Reagents and Equipment

[Samples]

Sodium butyrate (FUJIFILM Wako Pure Chemical Corporation) was dissolved in physiological saline to prepare a 10 mM sodium butyrate aqueous solution. The solution was sequentially diluted with physiological saline to prepare a dilution series containing sodium butyrate at concentrations of 0.156, 0.313, 0.625, 1.25, 2.5 and 5.0 mM. The physiological saline was used as a control sample containing no butyric acid.

[Composition of First Reagent]

100 mM Tris-HCl (pH 7.5) (Sigma-Aldrich Co. LLC.)

2 mM ATP (pH 7.5) (Oriental Yeast Co., Ltd.)

2 mM $MgCl_2$ (FUJIFILM Wako Pure Chemical Corporation)

20 mM glucose (Wako Pure Chemical Industries, Ltd.)

1 mM NADP (FUJIFILM Wako Pure Chemical Corporation)

5 U/mL G6PDH II (T-51, ASAHI KASEI PHARMA CORPORATION)

5 U/mL ADP-HK II (T-92, ASAHI KASEI PHARMA CORPORATION)

0.1% Triton (registered trademark) X-100 (NACALAI TESQUE, INC.)

[Composition of Second Reagent]

100 mM Tris-HCl (pH 7.5) (Sigma-Aldrich Co. LLC.)

10 mM KCl (FUJIFILM Wako Pure Chemical Corporation)

40 U/mL BKII

[Measurement Parameters of Automatic Analyzer]

Analysis method: 2 points

Measurement wavelength (secondary/primary): 700 nm/340 nm

Reaction time: 5 minutes

Photometry point: 16 to 34

Sample volume: 3.5 μL
First reagent amount: 140 μL
Second reagent amount: 35 μL
(3) Measurement of Butyric Acid The first reagent was dispensed into a cuvette, then the sample was added and stirred. Then, the second reagent was added to the cuvette and stirred. The mixed solution of the sample, the first reagent, and the second reagent was incubated at 37° C. for 5 minutes. After the addition of the second reagent, the cuvette was irradiated with light, and the change in absorbance at 340 nm for 5 minutes was measured. These operations were performed by the automatic analyzer. The results are shown in Table 2 and FIG. 14

TABLE 2

| Butyric acid (mM) | Abs 340 nm |
| --- | --- |
| 0.000 | 0.0000 |
| 0.156 | 0.0184 |
| 0.313 | 0.0370 |
| 0.625 | 0.0740 |
| 1.250 | 0.1481 |
| 2.500 | 0.2938 |
| 5.000 | 0.5834 |
| 10.000 | 1.1491 |

Figure 14:
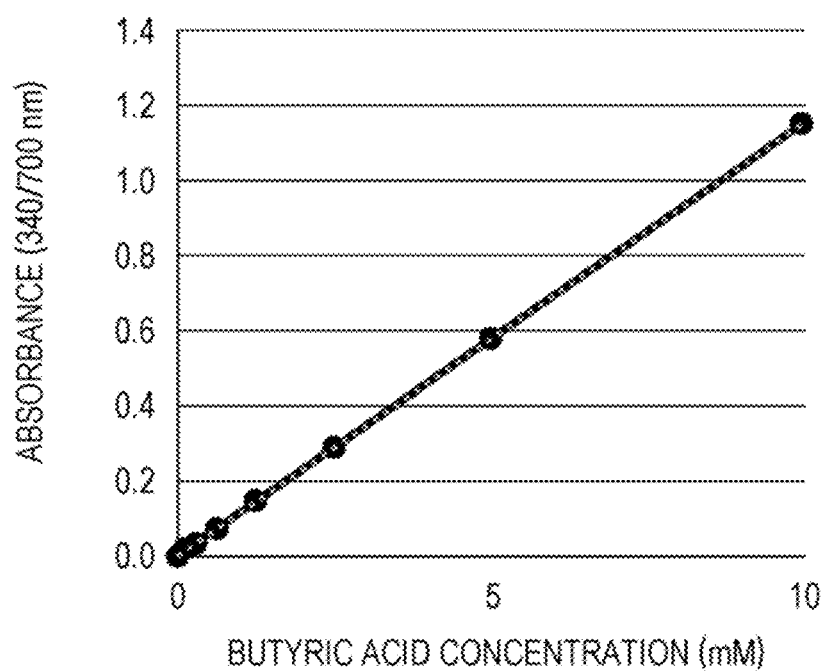
FIG. 14 is a graph showing the linearity of butyric acid quantification by the method for measuring butyric acid of the present embodiment.

As shown in FIG. 14, linearity up to a butyric acid concentration of 10 mM could be confirmed. Therefore, it was shown that the enzymatic measurement method of the present embodiment is capable of quantitative analysis of butyric acid. From Reference Example 7, the optimum pH of BKII is 8 to 9, but even when the pH of the second reagent containing BKII was adjusted to 7.5, there was no problem in the measurement.

Example 3: Measurement of Butyric Acid in Human Saliva

A bacterium that causes periodontal disease, such as *Porphyromonas gingivalis*, are known to release a short-chain fatty acid having 3 to 6 carbon atoms, especially butyric acid, in an oral cavity. It is known that about 3 to 4 mM butyric acid is also detected in the gingival crevicular fluid of a healthy subject. Therefore, it was examined whether a short-chain fatty acid having 3 to 6 carbon atoms in human saliva could be measured by the enzymatic measurement method of the present embodiment. The measurement was performed by a 7180 type Hitachi automatic analyzer (Hitachi High-Tech Corporation) or a hand method using a 96-well microplate. For comparison, a short-chain fatty acid was also measured by GC-MS.

In the measurement of a short-chain fatty acid by GC-MS, sodium acetate, sodium propionate, sodium butyrate, valeric acid, and sodium isovalerate manufactured by FUJIFILM Wako Pure Chemical Corporation, sodium isobutyrate manufactured by NACALAI TESQUE, INC., and sodium caproate manufactured by Sigma-Aldrich Co. LLC. were used as the standard solution. C13 isotope sodium acetate manufactured by Cambridge Isotope Lab. was used as an isotope internal standard substance mixed solution, and for propionic acid, butyric acid, isobutyric acid, caproic acid, and valeric acid manufactured by Sigma-Aldrich Co. LLC., deuterium substitutions were used. Before the measurement, an internal standard solution was added to each fatty acid, diethyl ether was added under hydrochloric acid acidity, the mixed solution was stirred, and then centrifuged. The ether layer of the supernatant was collected, tert-butyldimethyl-chlorosilane (Tokyo Chemical Industry Co., Ltd.) was added, and the mixed solution was heated at 60° C. for 30 minutes to prepare a GC-MS measurement sample. GCMS-QP2010 Ultra (SHIMADZU CORPORATION) was used for the analysis.

(1) Sample

Saliva was collected from 7 healthy subjects using a saliva collection set for periodontal disease saliva test (product code TZ1000, EIKEN CHEMICAL CO., LTD.). The collected saliva was centrifuged at 10,000 rpm for 10 minutes, and the supernatant was used as a sample. Although various short-chain fatty acids are contained in saliva, it is unknown which a short-chain fatty acid is specifically contained. Therefore, a solution containing butyric acid (called a butyric acid standard solution) as a representative of a short-chain fatty acid having 3 to 6 carbon atoms was used as the standard solution for creating the calibration curve. As the butyric acid standard solution, a 5.0 mM sodium butyrate aqueous solution was prepared. The physiological saline was used as a control sample containing no a short-chain fatty acid having 3 to 6 carbon atoms.

(2) Ultraviolet Part Measurement by Automatic Analyzer
(2.1) Reagents and Equipment The composition of the first reagent was the same as that of the first reagent used for examining the substrate specificity of Reference Example 7.
[Composition of Second Reagent]
100 mM Tris-HCl (pH 7.5) (Sigma-Aldrich Co. LLC.)
40 U/mL BKIII
[Measurement Parameters of Automatic Analyzer]
Analysis method: 2 points
Measurement wavelength (secondary/primary): 700 nm/340 nm
Reaction time: 5 minutes
Photometry point: 16 to 34
Sample volume: 3.5 μL
First reagent amount: 140 μL
Second reagent amount: 35 μL
(2.2) Measurement of a Short-Chain Fatty Acid Having 3 to 6 Carbon Atoms The first reagent was dispensed into a cuvette, then the sample was added and incubated at 37° C. for 5 minutes to measure the absorbance. After the addition of the second reagent, the mixed solution was incubated for 5 minutes and the absorbance was measured to determine the difference between the two absorbances. These operations were performed by the automatic analyzer. From the measurement results of the 5 mM butyric acid standard solution, the total amount of a short-chain fatty acid having 3 to 6 carbon atoms per unit volume in saliva was determined. The obtained value was used as the concentration of a short-chain fatty acid having 3 to 6 carbon atoms in saliva.

(3) Visible Part Measurement by the Hand Method Using a 96-Well Microplate
(3.1) Reagents
[Composition of First Reagent]
100 mM Tris-HCl (pH 7.5) (Sigma-Aldrich Co. LLC.)
2 mM KCl (FUJIFILM Wako Pure Chemical Corporation)
2 mM ATP (pH 7.5) (Oriental Yeast Co., Ltd.)
2 mM $MgCl_2$ (FUJIFILM Wako Pure Chemical Corporation)
20 mM glucose (FUJIFILM Wako Pure Chemical Corporation)
1 mM NADP (Oriental Yeast Co., Ltd.)
5 U/mL G6PDH II (T-51, ASAHI KASEI PHARMA CORPORATION)

5 U/mL ADP-HK II (T-92, ASAHI KASEI PHARMA CORPORATION)
8 U/mL BKIII 0.4 mM WST-1 (DOJINDO LABORATORIES)
1.6 U/mL diaphorase (T-06 or T-10, ASAHI KASEI PHARMA CORPORATION)
[Composition of Second Reagent]
1% Lithium dodecyl sulfate (FUJIFILM Wako Pure Chemical Corporation)
1% Triton (registered trademark) X-100 (NACALAI TESQUE, INC.)

(3.2) Measurement of a Short-Chain Fatty Acid Having 3 to 6 Carbon Atoms

A sample (5 μL) was added to each well of a 96-well microplate for ELISA (Nunc), then a first reagent (170 μL) was added and reacted at room temperature (about 20° C.) for 5 minutes. Then, a second reagent (20 μL) was added to each well to stop the reaction. The microplate was set on a plate reader Infinite 200 (Tecan Trading AG), and the absorbance of the reaction mixed solution in each well at 450 nm was measured. A calibration curve was created from the measurement results of the sodium butyrate aqueous solution to determine the concentration of a short-chain fatty acid having 3 to 6 carbon atoms in saliva. The same sample was measured by GC-MS, and calibration curves were created for each of the short-chain fatty acids other than acetic acid, namely propionic acid, butyric acid, isobutyric acid, valeric acid, isovaleric acid, and caproic acid to measure the individual concentrations (mM), and the total was taken as the concentration of a short-chain fatty acid having 3 to 6 carbon atoms.

(4) Results

Table 3 shows the measurement results by the automatic analyzer, the hand method, and GC-MS. The numerical values in the table are the concentrations (mM) of a short-chain fatty acid obtained from the calibration curve. These measurement results were plotted to confirm the correlation with the measurement by the automatic analyzer, the hand method, and the measurement by GC-MS. The results are shown in FIGS. 15A to 15C.

TABLE 3

| Sample number | Automatic analysis | Hand method | GC-MS |
|---|---|---|---|
| 1 | 1.22 | 1.40 | 0.80 |
| 2 | 0.50 | 0.69 | 0.42 |
| 3 | 1.67 | 1.76 | 1.08 |
| 4 | 0.64 | 0.87 | 0.46 |
| 5 | 0.13 | 0.49 | 0.19 |
| 6 | 3.67 | 4.06 | 1.70 |
| 7 | 3.06 | 3.74 | 2.37 |

Figure 15A:
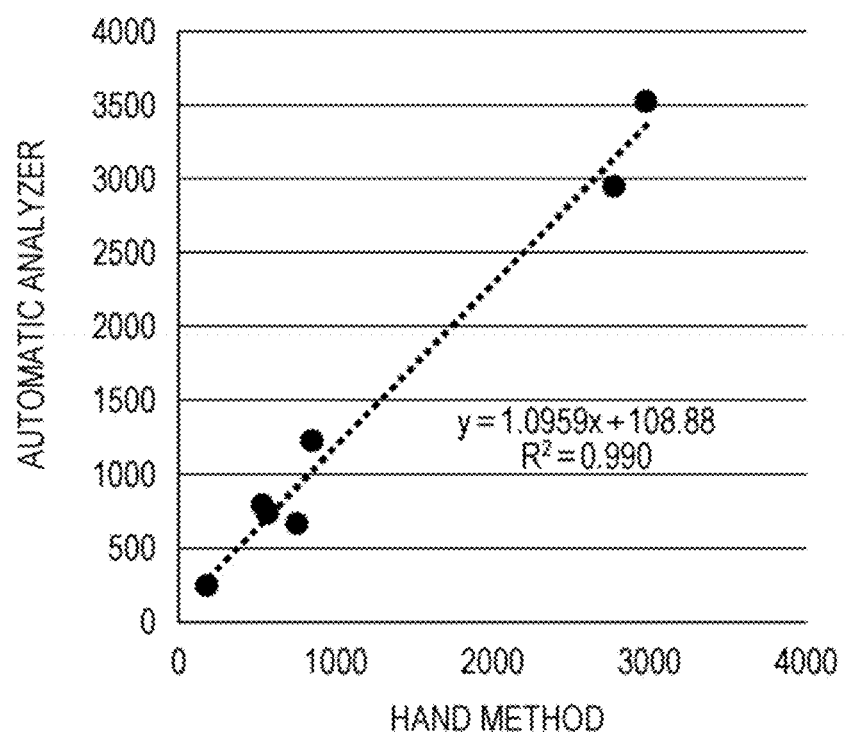
FIG. 15A is a graph showing the correlation between the measurement result by an automatic analyzer and the measurement result by a hand method.
Figure 15B:
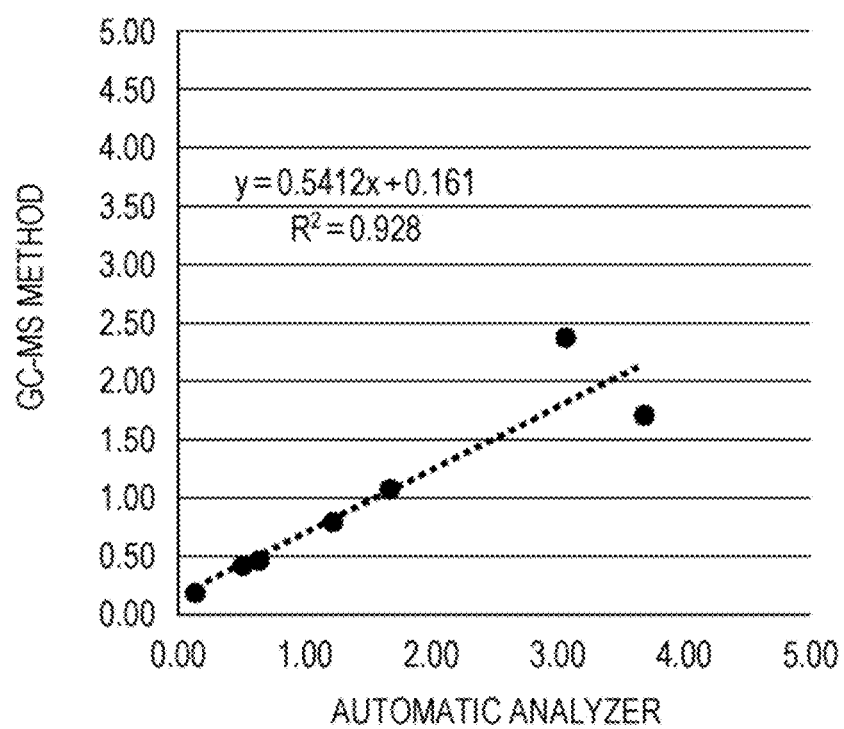
FIG. 15B is a graph showing the correlation between the measurement result by a GS-MS method and the measurement result by the automatic analyzer.
Figure 15C:
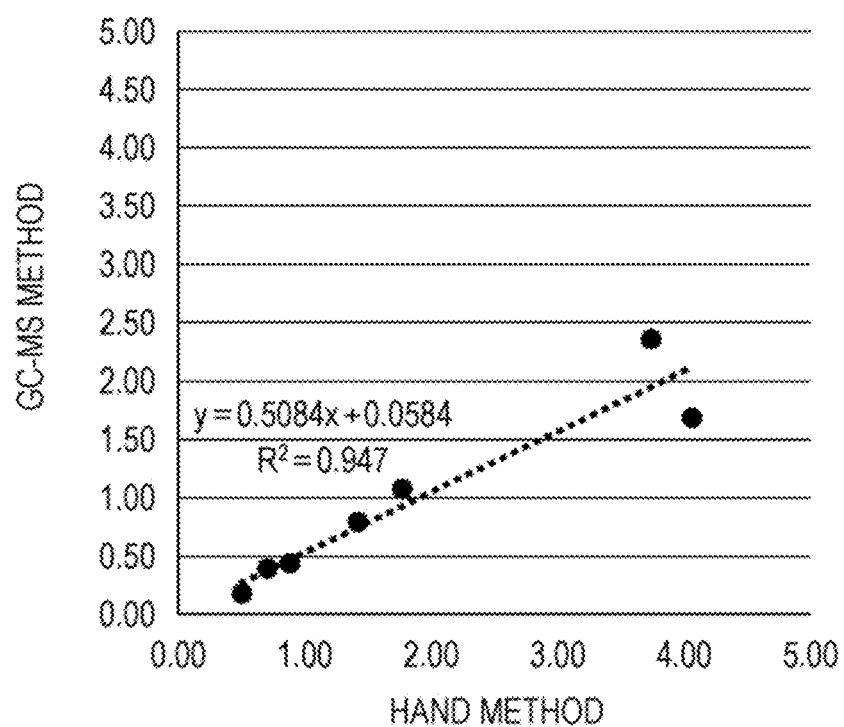
FIG. 15C is a graph showing the correlation between the measurement result by the GS-MS method and the measurement result by the hand method.

The correlation coefficient R between the automatic analysis method by the enzymatic method and the hand method was 0.990, and the regression formula was y=1.0959x+108.88 (see FIG. 15A). Therefore, the correlation between the measurement by the automatic analyzer and the measurement by the hand method was good. As described above, it was shown that almost the same measured value can be obtained by the enzymatic measurement method of the present embodiment regardless of whether the method is then automatic analyzer or the hand method. Next, the correlation coefficient R between the GC-MS method and the automatic analyzer was 0.928, and the regression formula was y=0.5412x+0.161 (see FIG. 15B). The correlation coefficient R between the GC-MS method and the hand method was 0.947, and the regression formula was y=0.5084x+0.0584 (see FIG. 15C). The correlation between GC-MS and enzymatic method was good.

Comparative Example 1: Measurement Using Acetate Kinase and Propionic Acid Kinase It was examined whether butyric acid could be measured by using acetate kinase (AK) or propionic acid kinase (PK) instead of butyrate kinase. For comparison, measurement using BKIII was also performed.

(1) Samples, Reagents and Equipment

[Samples]

Neutralized 100 mM acetic acid, butyric acid, and isobutyric acid were mixed with physiological saline to prepare a 5 mM acetic acid aqueous solution, a 5 mM butyric acid aqueous solution, and a 5 mM isobutyric acid aqueous solution, respectively.

The composition of the first reagent was the same as that of the first reagent used for examining the substrate specificity of Reference Example 7.

[Second Reagent]

AK (Sigma-Aldrich Co. LLC., derived from *E. coli*), PK (MyBioSource, recombinant protein) and BKIII were added to 100 mM Tris-HCl (pH 7.5) (Sigma-Aldrich Co. LLC.), respectively, to prepare an enzyme solution containing each enzyme at a concentration of 1.25 to 40 U/mL.

[Automatic Analyzer]

The measurement was performed using a 7180 type Hitachi automatic analyzer (Hitachi High-Tech Corporation). The measurement parameters of the automatic analyzer were the same as in Example 2.

(2) Measurement

In the same manner as in Example 2, butyric acid and isobutyric acid in the sample were measured by the automatic analyzer. The reaction recovery rate (%) was calculated by dividing the measured value by the theoretical absorbance value. The theoretical absorbance is the absorbance when all the substrate (butyric acid or isobutyric acid) in the sample is converted to NADPH, and is calculated by the following formula. Table 4 shows the reaction recovery rate (%) calculated from each measured value.

(Theoretical absorbance)=

(substrate concentration in sample)×[(sample volume)/(sample volume+ first reagent amount+second reagent amount)]×(NADPH millimole molecular extinction coefficient at 340 nm)=

5×[3.5/(3.5+140+35)]×6.3=

0.617

TABLE 4

| | AK activity value in reaction mixed solution (U/mL) | | | | | |
|---|---|---|---|---|---|---|
| Substrate | 0.3 | 0.5 | 1.0 | 2.0 | 4.0 | 8.0 |
| Acetic acid | 16 | 28 | 44 | 62 | 78 | 88 |
| Butyric acid | 0 | 0 | 0 | 0 | 0 | 0 |
| Isobutyric acid | 0 | 0 | 0 | 0 | 0 | 0 |

TABLE 4-continued

| | PK activity value in reaction mixed solution (U/mL) | | | | | |
|---|---|---|---|---|---|---|
| Substrate | 0.3 | 0.5 | 1.0 | 2.0 | 4.0 | 8.0 |
| Acetic acid | 0 | 2 | 3 | 9 | 21 | 39 |
| Butyric acid | 0 | 0 | 0 | 2 | 4 | 8 |
| Isobutyric acid | 0 | 0 | 0 | 0 | 0 | 0 |

| | BKIII activity value in reaction mixed solution (U/mL) | | | | | |
|---|---|---|---|---|---|---|
| Substrate | 0.3 | 0.5 | 1.0 | 2.0 | 4.0 | 8.0 |
| Acetic acid | 0 | 0 | 0 | 0 | 1 | 2 |
| Butyric acid | 36 | 53 | 70 | 84 | 93 | 98 |
| Isobutyric acid | 40 | 55 | 70 | 83 | 91 | 96 |

As shown in Table 4, it was shown that acetate kinase reacts with acetic acid but does not react with butyric acid and isobutyric acid. It was shown that propionic acid kinase reacts with acetic acid and hardly reacts with butyric acid and does not react with isobutyric acid. Therefore, it was shown that butyric acid and isobutyric acid cannot be measured using acetate kinase and propionic acid kinase. On the other hand, in the measurement using butyrate kinase, the reaction recovery rate of butyric acid and isobutyric acid increased depending on the concentration of butyrate kinase without reacting with acetic acid.

Comparative Example 2: Measurement Using Acetate-CoA Transferase

Acetate-CoA transferase (EC 2.8.3.8) has been reported to catalyze the reaction represented by the following formula (9) (EC 2.8.3.8 in the Enzyme nomenclature database on the ExPASy-SIB Bioinformatics Resource Portal).). It was examined whether butyric acid could be measured by the reaction of formula (10), which is the reverse reaction of formula (9), using acetate-CoA transferase instead of butyrate kinase The acetic acid produced by the formula (10) by acetate-CoA transferase was confirmed by the reaction with AK of Comparative Example 1. The measurement was performed using a 7180 type Hitachi automatic analyzer (Hitachi High-Tech Corporation).

[Chemical formula 7]

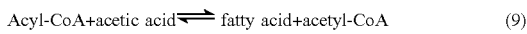

Acyl-CoA+acetic acid $\rightleftharpoons$ fatty acid+acetyl-CoA  (9)

Butyric acid+acetyl-CoA→butyrate-CoA+acetic acid  (10)

(1) Samples, Reagents and Equipment
[Samples]
The 5 mM butyric acid and 5 mM isobutyric acid aqueous solution used in Comparative Example 1 were used.
[Composition of First Reagent]
100 mM Tris-HCl (pH 7.5) (Sigma-Aldrich Co. LLC.)
2 mM MgCl$_2$ (FUJIFILM Wako Pure Chemical Corporation)
2 mM ATP (pH 7.5) (Oriental Yeast Co., Ltd.)
20 mM glucose (FUJIFILM Wako Pure Chemical Corporation)
1 mM NADP (FUJIFILM Wako Pure Chemical Corporation)
5 U/mL G6PDH II (Glucose-6-phosphate dehydrogenase: T-51, ASAHI KASEI PHARMA CORPORATION)
5 U/mL ADP-HK II (ADP dependent hexokinase: T-92, ASAHI KASEI PHARMA CORPORATION)
1.25 mM Acetyl-CoA (Sigma-Aldrich Co. LLC.)
20 U/mL AK (Sigma-Aldrich Co. LLC.)

[Second Reagent]
30 μg/mL acetate-CoA transferase (from MyBioSource, derived from *E. coli*)
100 mM Tris-HCl (pH 7.5) (Sigma-Aldrich Co. LLC.)
[Automatic Analyzer]
The measurement was performed using a 7180 type Hitachi automatic analyzer (Hitachi High-Tech Corporation). The measurement parameters of the automatic analyzer were the same as in Example 2.
(2) Measurement
In the same manner as in Example 2, butyric acid and isobutyric acid in the sample were measured by the automatic analyzer. The reaction recovery rate (%) was calculated by dividing the measured value by the theoretical absorbance value of Comparative Example 1.

TABLE 5

| Substrate | Reaction recovery rate (%) |
|---|---|
| Butyric acid | 3 |
| Isobutyric acid | 4 |

As shown in Table 5, it was shown that acetate-CoA transferase has little reaction to butyric acid and isobutyric acid. It was considered that a reverse reaction was less reactive than a positive reaction.

Comparative Example 3: Measurement Using Butyrate-Acetoacetate-CoA Transferase

Butyrate-acetoacetate-CoA transferase (EC 2.8.3.9) catalyzes the reaction represented by the following formula (11) (EC 2.8.3.9 in the Enzyme nomenclature database on the ExPASy-SIB Bioinformatics Resource Portal). It was examined whether acetic acid and butyric acid could be measured by the reaction of formula (12), which is the reverse reaction of the formula (11), using butyrate-acetoacetate-CoA transferase instead of butyrate kinase. As represented by the formula (12), acetoacetic acid is produced by butyrate-acetoacetate-CoA transferase. The produced acetoacetic acid was confirmed by a reduction reaction of β-NADH by 3-hydroxybutyrate dehydrogenase represented by formula (13). The measurement was performed using a 7180 type Hitachi automatic analyzer (Hitachi High-Tech Corporation).

[Chemical formula 8]

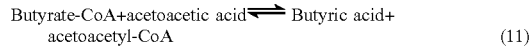

Butyrate-CoA+acetoacetic acid $\rightleftharpoons$ Butyric acid+ acetoacetyl-CoA  (11)

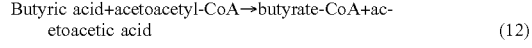

Butyric acid+acetoacetyl-CoA→butyrate-CoA+acetoacetic acid  (12)

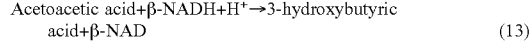

Acetoacetic acid+β-NADH+H$^+$→3-hydroxybutyric acid+β-NAD  (13)

(1) Samples, Reagents and Equipment
[Samples]
The 5 mM acetic acid aqueous solution, 5 mM butyric acid aqueous solution, and 5 mM isobutyric acid aqueous solution used in Comparative Example 1 were used.
[Composition of First Reagent]
100 mM Tris-HCl (pH 7.5) (Sigma-Aldrich Co. LLC.)
0.35 mM Acetoacetyl-CoA (Sigma-Aldrich Co. LLC.)
2 mM MgCl$_2$ (FUJIFILM Wako Pure Chemical Corporation)
0.25 mM β-NADH (Oriental Yeast Co., Ltd.)

5 U/mL 3-hydroxybutyrate dehydrogenase (FUJIFILM Wako Pure Chemical Corporation)

[Second Reagent]

60 µg/mL butyrate-acetoacetate-CoA transferase (from MyBioSource, derived from *E. coli*)

100 mM Tris-HCl (pH 7.5) (Sigma-Aldrich Co. LLC.)

[Automatic Analyzer]

The measurement was performed using a 7180 type Hitachi automatic analyzer (Hitachi High-Tech Corporation). The measurement parameters of the automatic analyzer were the same as in Example 2.

(2) Measurement

In the same manner as in Example 2, acetic acid, butyric acid, and isobutyric acid in the sample were measured by the automatic analyzer. The reaction recovery rate (%) was calculated by dividing the measured value by the theoretical absorbance value of Comparative Example 1. However, since the product was produced twice in the reaction of Comparative Example 3, it was divided by 2.

TABLE 6

| Substrate | Reaction recovery rate (%) |
|---|---|
| Acetic acid | 1 |
| Butyric acid | 2 |
| Isobutyric acid | 2 |

As shown in Table 6, it was shown that butyrate-acetoacetate-CoA transferase has little reaction to butyric acid and isobutyric acid. It is considered that a reverse reaction was less reactive than a positive reaction. It is also reported that EC 2.8.3.9 of the Enzyme nomenclature database on the ExPASy-SIB Bioinformatics Resource Portal reacts slowly to a short-chain fatty acid with 2 to 6 carbon atoms (C2-C6).

Comparative Example 4: Measurement Using 2-Enoate Reductase

EC 1.3.1.31, that is, 2-Enoate reductase catalyzes the reaction represented by the following formula (14) (EC 1.3.1.31 of the Enzyme nomenclature database in the ExPASy-SIB Bioinformatics Resource Portal). In order to examine whether butyric acid can be measured by using 2-enoate reductase instead of butyrate kinase, it was confirmed whether 2-enoate reductase causes the reaction represented by the formula (15). The measurement was performed using a 7080 type Hitachi automatic analyzer (Hitachi High-Tech Corporation).

[Chemical formula 9]

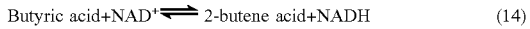

Butyric acid+NAD$^+$ ⇌ 2-butene acid+NADH        (14)

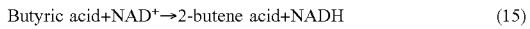

Butyric acid+NAD$^+$ → 2-butene acid+NADH        (15)

(1) Preparation of 2-Enoate Reductase Derived from *Meiothermus silvanus*

Figure 16:
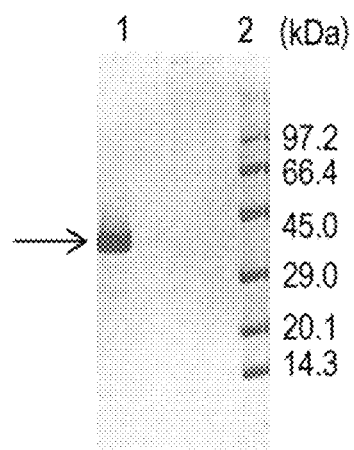
FIG. 16 is a diagram showing the result of analysis of a solution of recombinant 2-enoate reductase derived from *Meiothermus silvanus* by SDS-PAGE.

Chromosomal DNA was prepared by a conventional method from *Meiothermus silvanus* (DSM No. 9946, DSMZ). Using the obtained chromosomal DNA as a template, PCR was performed using a sense primer (SEQ ID NO: 12), an antisense primer (SEQ ID NO: 13), and KOD FX (product number: KFX-101, TOYOBO CO., LTD.), and a 2-enoate reductase gene was amplified to obtain a PCR product of about 1100 bp. The obtained PCR product was digested with NdeI (Takara Bio Inc.) and HindIII (Takara Bio Inc.), inserted into the NdeI-HindIII site of the pET-21a (+) vector (Novagen), and MsER/pET21a(+) expression plasmid was obtained. In the expression plasmid, a vector-derived linker and a base sequence encoding His tag were added to the 3' end of the 2-enoate reductase. That is, the MsER/pET21a(+) expression plasmid contained a polynucleotide encoding a 2-enoate reductase-linker-His tag. The expression plasmid was introduced into One shot BL21 (DE3) Chemically Competent *E. coli* (Invitrogen) to obtain a transformant MsER/pET-21a(+)/BL21(DE3) having a recombinant vector containing a polynucleotide encoding 2-enoate reductase derived from *Meiothermus silvanus*. The obtained transformant was cultured in the same manner as in Reference Example 1, and a crude enzyme solution was prepared from the bacterial cell. The obtained crude enzyme solution was purified in the same manner as in Reference Example 1 to obtain a solution of recombinant 2-enoate reductase. A part of the obtained butyrate kinase solution was taken and analyzed by SDS-PAGE. The results are shown in FIG. 16 In the drawing, a lane 1 shows the enzyme solution, a lane 2 shows the molecular weight marker, and the arrow shows the band corresponding to 2-enoate reductase.

(2) Preparation of 2-Enoate Reductase Derived from *Kluyveromyces lactis*

Figure 17:
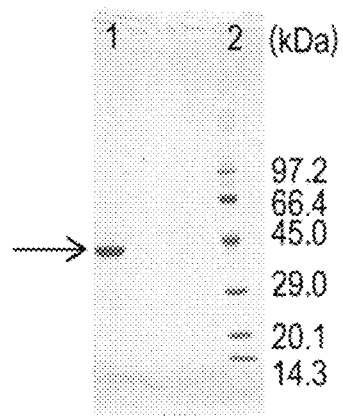
FIG. 17 is a diagram showing the results of analysis of a solution of recombinant 2-enoate reductase derived from *Kluyveromyces lactis* by SDS-PAGE.

Chromosomal DNA was prepared by a conventional method from *Kluyveromyces lactis* (DSM No. 70799, DSMZ). Using the obtained chromosomal DNA as a template, PCR was performed using a sense primer (SEQ ID NO: 14), an antisense primer (SEQ ID NO: 15), and KOD FX (product number: KFX-101, TOYOBO CO., LTD.), and the 2-enoate reductase gene was amplified to obtain a PCR product of about 1200 bp. The obtained PCR product was digested with NdeI (Takara Bio Inc.) and XhoI (Takara Bio Inc.), inserted into the NdeI-XhoI site of the pET-21a(+) vector (Novagen), and KlER/pET21a(+) expression plasmid was obtained. In the expression plasmid, a vector-derived linker and a base sequence encoding His tag were added to the 3' end of the 2-enoate reductase. That is, the KlER/pET21a(+) expression plasmid contained a polynucleotide encoding a 2-enoate reductase-linker-His tag. The expression plasmid was introduced into One shot BL21(DE3) Chemically Competent *E. coli* (Invitrogen), and a transformant KlER/pET-21a(+)/BL21(DE3) having a recombinant vector containing a polynucleotide encoding a 2-enoate reductase derived from *Kluyveromyces lactis*. The obtained transformant was cultured in the same manner as in Reference Example 1, and a crude enzyme solution was prepared from the bacterial cell. The obtained crude enzyme solution was purified in the same manner as in Reference Example 1 to obtain a solution of recombinant 2-enoate reductase. A part of the obtained butyrate kinase solution was taken and analyzed by SDS-PAGE. The results are shown in FIG. 17 In the drawing, a lane 1 shows the enzyme solution, a lane 2 shows the molecular weight marker, and the arrow shows the band corresponding to 2-enoate reductase.

(3) Measurement Based on Change in Absorbance by NADH or NADPH (3.1) Reagent and Equipment

[Composition of First Reagent]

100 mM Tris-HCl (Sigma-Aldrich Co. LLC.)

3 mM NAD or NADP (FUJIFILM Wako Pure Chemical Corporation)

150 mM butyric acid (FUJIFILM Wako Pure Chemical Corporation)

The pH of the first reagent was adjusted to 7.5, 8, 8.5 or 9 with 5 N hydrochloric acid.

[Measurement Parameters of Automatic Analyzer]
Analysis method: Rate-A
Measurement wavelength (secondary/main): none/340 nm
Reaction time: 5 minutes
Photometry point: 10-15
Sample volume: 3 μL
First reagent amount: 150 μL (3.2) Measurement of Enzymatic Activity A solution of recombinant 2-enoate reductase derived from *Meiothermus silvanus* and *Kluyveromyces lactis* was used as a sample. The first reagent was dispensed into a cuvette, then the sample was added and stirred. The mixed solution of the sample and the first reagent was incubated at 37° C. for 5 minutes. After the addition of the sample, the cuvette was irradiated with light and the absorbance at 340 nm was measured. These operations were performed by the automatic analyzer. As a result of the measurement, the absorbance at 340 nm did not increase. This indicates that NADH or NADPH was not produced. Therefore, the reaction represented by the formula (15) could not be confirmed.

(4) Measurement Based on the Production of Formazan Dye (4.1) Reagents and Equipment

[Composition of First Reagent]
100 mM Tris-HCl (Sigma-Aldrich Co. LLC.)
0.1% bovine serum albumin (product number: 10416-59-8, Tokyo Chemical Industry Co., Ltd.)
0.03% nitroblue tetrazolium (product number No. 298-83-9: Tokyo Chemical Industry Co., Ltd.)
3 mM NAD or NADP (FUJIFILM Wako Pure Chemical Corporation)
50 mM butyric acid (FUJIFILM Wako Pure Chemical Corporation)
10 U/mL diaphorase (T-06 or T-10, ASAHI KASEI PHARMA CORPORATION)

The pH of the first reagent was adjusted to 7.5, 8, 8.5 or 9 with 5 N hydrochloric acid.

[Measurement Parameters of Automatic Analyzer]
Analysis method: Rate-A
Measurement wavelength (secondary/main): none/546 nm
Reaction time: 5 minutes
Photometry point: 10-15
Sample volume: 3 μL
First reagent amount: 150 μL (4.2) Measurement of Enzymatic Activity A solution of recombinant 2-enoate reductase derived from *Meiothermus silvanus* and *Kluyveromyces lactis* was used as a sample. The first reagent was dispensed into a cuvette, then the sample was added and stirred. The mixed solution of the sample and the first reagent was incubated at 37° C. for 5 minutes. After the addition of the sample, the cuvette was irradiated with light and the absorbance at 546 nm was measured. These operations were performed by the automatic analyzer. As a result of the measurement, the absorbance at 546 nm did not increase. This indicates that nitroblue tetrazolium was not converted to a formazan dye. Therefore, the reaction represented by the formula (15) could not be confirmed.

From the above measurement results, it was shown that the recombinant 2-enoate reductase derived from *Meiothermus silvanus* and *Kluyveromyces lactis* does not catalyze the reaction represented by the formula (15). Therefore, it was shown that butyric acid cannot be measured using 2-enoate reductase.

Example 4: Measurement of Butyric Acid in Swine Feces

Butyric acid, which is mainly produced by gut flora belonging to Clostridiales, is known to promote differentiation into a regulatory T cell (Treg) that control immune tolerance. Therefore, it was examined whether butyric acid in swine feces could be measured by the enzymatic measurement method of the present embodiment. The measurement was performed using a 7180 type Hitachi automatic analyzer (Hitachi High-Tech Corporation). For comparison, measurement of a short-chain fatty acid by GC-MS was performed under the same conditions as in Example 3.

(1) Sample

PBS buffer (4 mL) was added to feces of 6 swines (1 g each), and the mixture was dispersed and stirred with a mixer. The feces dispersion was centrifuged at 5,000 G for 20 minutes, and 3 mL of the supernatant was collected. The obtained supernatant was filtered through a 0.8 μm filter to prepare a sample. As the butyric acid standard solution, a 5.0 mM sodium butyrate aqueous solution was prepared. The physiological saline was used as a control sample containing no butyric acid.

(2) Ultraviolet Part Measurement by Automatic Analyzer

Since the myokinase activity is high in the feces and the sample is turbid, the myokinase inhibitor Ap5A was added to the first reagent used for examining the substrate specificity of Reference Example 7 so as to be 50 μM, and Triton (trademark) X-100 was added to a concentration of 0.1% to remove turbidity. The obtained reagent was used as the first reagent of Example 4. As the second reagent, the second reagent of Example 3 was used. The measurement by the 7180 Hitachi automatic analyzer was performed in the same manner as in Example 3 with the same measurement parameters as in Example 3.

(3) Results

Figure 18:
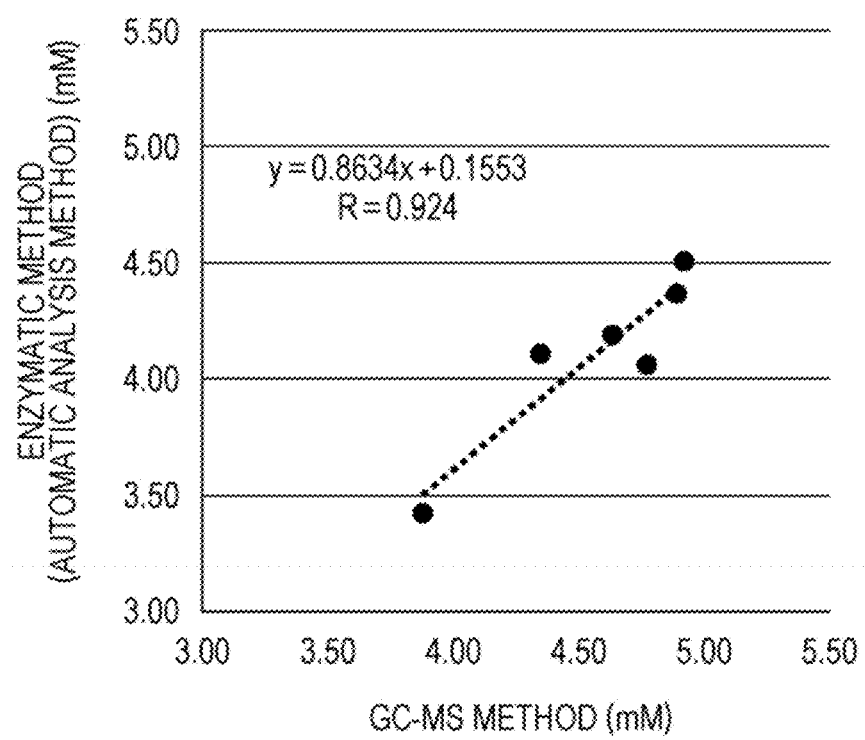
FIG. 18 is a graph showing the correlation between the measurement result by the GS-MS method and the measurement result by the automatic analyzer.

FIG. 18 shows the results of enzymatic measurement by the 7180 Hitachi automatic analyzer and GC-MS measurement. Since the regression formula was y=0.8634x+0.1553 and the correlation coefficient was 0.924, a good correlation between GC-MS and enzymatic measurement was obtained.

What is claimed is:

1. A method for measuring the amount of a short-chain fatty acid having 3 to 6 carbon atoms in a sample, comprising:

enzymatically reacting the short-chain fatty acid with adenosine triphosphate (ATP), and a butyrate kinase such that adenosine diphosphate (ADP) is produced, and measuring the amount of ADP produced;

wherein said short-chain fatty acid is at least one selected from the group consisting of propionic acid, butyric acid, isobutyric acid, valeric acid, isovaleric acid, and caproic acid, wherein the butyrate kinase is from *Acetoanaerobium sticklandii* or *Thermosediminibacter oceani*, and wherein the sample is at least one selected from the group consisting of saliva, gingival crevicular fluid, blood, plasma, serum and urine.

2. The method according to claim 1, wherein a measured value of the produced ADP indicates a total amount of the short-chain fatty acid having 3 to 6 carbon atoms in the sample, or a total amount of the short-chain fatty acid having 3 to 6 carbon atoms per unit volume.

3. The method according to claim 1, wherein the measuring the produced ADP comprises contacting the produced ADP with glucose; and ADP dependent hexokinase in a presence of a divalent metal ion to produce glucose-6-phosphate and adenosine monophosphate, and measuring the amount of glucose-6-phosphate produced.

4. The method according to claim 3, wherein the measuring the produced ADP further comprises:

contacting the produced glucose-6-phosphate with; nicotinamide adenine dinucleotide oxidized form (NAD) or nicotinamide adenine dinucleotide phosphate oxidized form (NADP), and glucose-6-phosphate dehydrogenase to produce 6-phosphoglucono-δ-lactone and nicotinamide adenine dinucleotide reduced form (NADH) or nicotinamide adenine dinucleotide phosphate reduced form (NADPH); and measuring the amount of NADH or NADPH produced.

5. The method according to claim 4, wherein the measuring the amount of NADH or NADPH produced is performed by measuring an absorbance or fluorescence intensity of a reaction mixed solution comprising the produced NADH or NADPH.

6. The method according to claim 4, wherein the measuring the produced NADH or NADPH is performed by contacting the produced NADH or NADPH, a coloring reagent, and an electron carrier to produce a dye, and measuring an absorbance of a reaction mixed solution comprising the produced dye.

7. The method according to claim 1, wherein producing ADP is performed by contacting the sample, the ATP, and the butyrate kinase in a presence of a divalent metal ion.

8. The method according to claim 7, wherein the divalent metal ion is at least one kind selected from the group consisting of a magnesium ion and a zinc ion.

9. The method according to claim 1, wherein the butyrate kinase comprises the amino acid sequence of SEQ ID NO:17 or 19.

* * * * *

SEQUENCE LISTING

<160> NUMBER OF SEQ ID NOS: 25

<210> SEQ ID NO 1
<211> LENGTH: 28
<212> TYPE: DNA
<213> ORGANISM: Artificial Sequence
<220> FEATURE:
<223> OTHER INFORMATION: Synthetic primer sequence

<400> SEQUENCE: 1
gggaattcat ggagggaact atgagcac                                        28

<210> SEQ ID NO 2
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 2
ggaagcttag cctcatatct ttgtggtttc                                      30

<210> SEQ ID NO 3
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 3
ggcatatgac gttttacggg atactggcga                                      30

<210> SEQ ID NO 4
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 4
gggaagcttt aaatactcct ttggcttttc                                      30

<210> SEQ ID NO 5
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 5
taagcttata aatactcctt tggcttttcc                                      30

<210> SEQ ID NO 6
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 6
tcatatggaa aagtttagga tactcgcaat                                      30

<210> SEQ ID NO 7
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 7
taagcttttc acctcccccg taatccagta                                      30

<210> SEQ ID NO 8
<211> LENGTH: 29
<212> TYPE: DNA

```
<213> ORGANISM: Artificial Sequence
<220> FEATURE:
<223> OTHER INFORMATION: Synthetic primer sequence

<400> SEQUENCE: 8
tcatatgaaa caagaacatc gcttgttag                                    29

<210> SEQ ID NO 9
<211> LENGTH: 29
<212> TYPE: DNA
<213> ORGANISM: Artificial Sequence
<220> FEATURE:
<223> OTHER INFORMATION: Synthetic primer sequence

<400> SEQUENCE: 9
ttaagcttag agtaatcttt cggagtttc                                    29

<210> SEQ ID NO 10
<211> LENGTH: 29
<212> TYPE: DNA
<213> ORGANISM: Artificial Sequence
<220> FEATURE:
<223> OTHER INFORMATION: Synthetic primer sequence

<400> SEQUENCE: 10
ttcatatgca gcagcgcctg ctgatcatc                                    29

<210> SEQ ID NO 11
<211> LENGTH: 29
<212> TYPE: DNA
<213> ORGANISM: Artificial Sequence
<220> FEATURE:
<223> OTHER INFORMATION: Synthetic primer sequence

<400> SEQUENCE: 11
ttaagcttct cgcctgcctc cccgtacac                                    29

<210> SEQ ID NO 12
<211> LENGTH: 29
<212> TYPE: DNA
<213> ORGANISM: Artificial Sequence
<220> FEATURE:
<223> OTHER INFORMATION: Synthetic primer sequence

<400> SEQUENCE: 12
cccatatgag tctgctgttc gagccgctc                                    29

<210> SEQ ID NO 13
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 13
ccaagcttgc cgggaaaagc ccggtcgtac                                   30

<210> SEQ ID NO 14
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 14
cccatatgtc gtttatgaac tttgaaccaa                                   30
```

<210> SEQ ID NO 15
<211> LENGTH: 29
<212> TYPE: DNA
<213> ORGANISM: Artificial Sequence
<220> FEATURE:
<223> OTHER INFORMATION: Synthetic primer sequence

<400> SEQUENCE: 15
ccctcgagtt tcttgtaacc cttggcaac                               29

<210> SEQ ID NO 16
<211> LENGTH: 1086
<212> TYPE: DNA
<213> ORGANISM: Acetoanaerobium sticklandii

<400> SEQUENCE: 16
atggagggaa ctatgagcac ttataaaata ttagctatta atccaggatc tacatcaaca     60
aagattgctg tatatgaaaa tgaaacacaa taatggaaa aaactctaag acattctaca    120
gaagaaatca ataaatacga gaaatctttt gatcaatttg aatttagaaa gaacgttata    180
gtagacgcag ttagtgaagc tggaattgct attgaagaac tagatgcagt agtaggaaga    240
ggaggccttt taaagccaat taaaggcgga acctatgaag tatctgatga actaattgct    300
ggacttaaag agccatacct tggagagcat gcttcgaatt taggcggaat catcgctaaa    360
gaaattgctg atgcagcact tgctccttca tttatagttg acccagtagt agttgatgaa    420
atgaatgatg tagctagaat ttcaggtatg ccagaaaatt ctagattctc aatattccat    480
gcactaaatc aaaaagctac agctagaaga tttgctagtg aaattggaaa atcatatgaa    540
gacataaatg taatcgtagc tcatatgggc ggaggagtat ctgtaggagc tcatgaaaaa    600
ggaagagtta tagatgtaaa taatgctcta gacggagaag gaccattttc accagaaaga    660
gctggaggac ttccagttgg agatttagct aagctatgct ttagtgggaa atatacacat    720
gcacaaatca gaagctatt aaaaggcgaa ggcggaatag tagcttattt aggaacaaat    780
gatgctagag atgttgaaaa gatgatagct gaaggcgacg aaaaggctaa actaatctac    840
gaagctatgg cttaccaagt tgcaaaggaa ataggttcat gcgctactgt acttaaaggt    900
aaggtagatg caattatcct tactggagga attgcatatt ctgaaatgat aactacatgg    960
attaaggaaa gagtatcatt tatagctgat gtaaaaatat atgctggtga ggatgaaatg   1020
tcagctctag ctcaaggagc acttcgtgtt cttcgtgagg aagagaaacc acaaagatat   1080
gaggct                                                              1086

<210> SEQ ID NO 17
<211> LENGTH: 362
<212> TYPE: PRT
<213> ORGANISM: Acetoanaerobium sticklandii

<400> SEQUENCE: 17

Met Glu Gly Thr Met Ser Thr Tyr Lys Ile Leu Ala Ile Asn Pro Gly
1               5                   10                  15

Ser Thr Ser Thr Lys Ile Ala Val Tyr Glu Asn Glu Thr Gln Ile Met
            20                  25                  30

Glu Lys Thr Leu Arg His Ser Thr Glu Glu Ile Asn Lys Tyr Glu Lys
        35                  40                  45

Ile Phe Asp Gln Phe Glu Phe Arg Lys Asn Val Ile Val Asp Ala Val
    50                  55                  60

Ser Glu Ala Gly Ile Ala Ile Glu Glu Leu Asp Ala Val Val Gly Arg
65                  70                  75                  80

Gly Gly Leu Leu Lys Pro Ile Lys Gly Thr Tyr Glu Val Ser Asp
                85                  90                  95

Glu Leu Ile Ala Gly Leu Lys Glu Pro Tyr Leu Gly Glu His Ala Ser
            100                 105                 110

Asn Leu Gly Gly Ile Ile Ala Lys Glu Ile Ala Asp Ala Ala Leu Ala
            115                 120                 125

Pro Ser Phe Ile Val Asp Pro Val Val Asp Glu Met Asn Asp Val
130                 135                 140

Ala Arg Ile Ser Gly Met Pro Glu Ile Pro Arg Phe Ser Ile Phe His
145                 150                 155                 160

Ala Leu Asn Gln Lys Ala Thr Ala Arg Arg Phe Ala Ser Glu Ile Gly
                165                 170                 175

Lys Ser Tyr Glu Asp Ile Asn Val Ile Val Ala His Met Gly Gly
            180                 185                 190

Val Ser Val Gly Ala His Glu Lys Gly Arg Val Ile Asp Val Asn Asn
            195                 200                 205

Ala Leu Asp Gly Glu Gly Pro Phe Ser Pro Glu Arg Ala Gly Gly Leu
210                 215                 220

Pro Val Gly Asp Leu Ala Lys Leu Cys Phe Ser Gly Lys Tyr Thr His
225                 230                 235                 240

Ala Gln Ile Lys Lys Leu Leu Lys Gly Glu Gly Ile Val Ala Tyr
                245                 250                 255

Leu Gly Thr Asn Asp Ala Arg Asp Val Glu Lys Met Ile Ala Glu Gly
            260                 265                 270

Asp Glu Lys Ala Lys Leu Ile Tyr Glu Ala Met Ala Tyr Gln Val Ala
            275                 280                 285

Lys Glu Ile Gly Ser Cys Ala Thr Val Leu Lys Gly Lys Val Asp Ala
            290                 295                 300

Ile Ile Leu Thr Gly Gly Ile Ala Tyr Ser Glu Met Ile Thr Thr Trp
305                 310                 315                 320

Ile Lys Glu Arg Val Ser Phe Ile Ala Asp Val Lys Ile Tyr Ala Gly
                325                 330                 335

Glu Asp Glu Met Ser Ala Leu Ala Gln Gly Ala Leu Arg Val Leu Arg
            340                 345                 350

Glu Glu Glu Lys Pro Gln Arg Tyr Glu Ala
            355                 360

<210> SEQ ID NO 18
<211> LENGTH: 1071
<212> TYPE: DNA
<213> ORGANISM: Thermosediminibacter oceani

<400> SEQUENCE: 18
atgacgtttt acgggatact ggcgattaat ccgggttcaa catccacgaa aatcgccgtc      60
tttgaaaacg aagaactaat atttgaggag aaaatcagcc attctaccga ggaactttca     120
aagtacgaca gcatattggc tcagtacccg ttcagaaaga agttaattct gaagtaata      180 gaacaaaagg gttataattt gagtaggctg aaggctgttg tcggccgcgg aggcctgctt     240
aaacctctgg agggtggcac ctacaccgtc aacgaacgga tgctggaaga cctcaaaaag     300
ggtgtgcagg gggaacacgc gtccaacctg gggggaatcc ttgcttacga ataggccgg      360 gaactgggag tgcccgcttt catagtagac ccggtggtgg tagacgaact ggaaccagtc     420

-continued

```
gccagaatta ccgggttgcc ggaaatagaa cggcgcagca tattccacgc tttgaaccag    480
aaagccgtag caagaagagt ggcaaagact ctaggcagga gttacgaaga gcttaacttg    540
atcgttgccc acctgggcgg aggaatcacc gtcggtgccc ataaaaaggg cagggtaatc    600
gatgtaaaca acggactgga cggtgaaggt ccgttctcac cggaaagggc agggcagttg    660
ccggcaatgg attttgcgaa actcattttt tctaaaaatc tgaccattca cgaaataaag    720
aaaatgttag ccggcaaagg gggccttgta gcccacttcg ggataaacga cgcccgggtt    780
ataaagaaga tgatagaaga gggcaaccaa gaagtaaggc tggtatacga agccatggct    840
taccaggtag ccaaggaaat aggagcatgc gcagcagtgc tttgcggtcg ggtggatgcg    900
gtagttctta ccggtggtct cgctcatgac gaaatgctgg tggactggat aaaaaacagg    960
gtttctttca tagctcctgt ttacgtcttc ccaggagaag acgaacttag agctcttgcc   1020
gaaggcgcat tgcgggtttt gaccggccag gaaaagccaa aggagtattt a            1071
```

<210> SEQ ID NO 19
<211> LENGTH: 357
<212> TYPE: PRT
<213> ORGANISM: Thermosediminibacter oceani

<400> SEQUENCE: 19

```
Met Thr Phe Tyr Gly Ile Leu Ala Ile Asn Pro Gly Ser Thr Ser Thr
1               5                   10                  15

Lys Ile Ala Val Phe Glu Asn Glu Glu Leu Ile Phe Glu Glu Lys Ile
            20                  25                  30

Ser His Ser Thr Glu Glu Leu Ser Lys Tyr Asp Ser Ile Leu Ala Gln
        35                  40                  45

Tyr Pro Phe Arg Lys Lys Leu Ile Leu Glu Val Ile Glu Gln Lys Gly
    50                  55                  60

Tyr Asn Leu Ser Arg Leu Lys Ala Val Val Gly Arg Gly Gly Leu Leu
65                  70                  75                  80

Lys Pro Leu Glu Gly Gly Thr Tyr Thr Val Asn Glu Arg Met Leu Glu
                85                  90                  95

Asp Leu Lys Lys Gly Val Gln Gly Glu His Ala Ser Asn Leu Gly Gly
            100                 105                 110

Ile Leu Ala Tyr Glu Ile Gly Arg Glu Leu Gly Val Pro Ala Phe Ile
        115                 120                 125

Val Asp Pro Val Val Asp Glu Leu Glu Pro Val Ala Arg Ile Thr
    130                 135                 140

Gly Leu Pro Glu Ile Glu Arg Arg Ser Ile Phe His Ala Leu Asn Gln
145                 150                 155                 160

Lys Ala Val Ala Arg Arg Val Ala Lys Thr Leu Gly Arg Ser Tyr Glu
                165                 170                 175

Glu Leu Asn Leu Ile Val Ala His Leu Gly Gly Gly Ile Thr Val Gly
            180                 185                 190

Ala His Lys Lys Gly Arg Val Ile Asp Val Asn Asn Gly Leu Asp Gly
        195                 200                 205

Glu Gly Pro Phe Ser Pro Glu Arg Ala Gly Gln Leu Pro Ala Met Asp
    210                 215                 220

Phe Ala Lys Leu Ile Phe Ser Lys Asn Leu Thr Ile His Glu Ile Lys
225                 230                 235                 240

Lys Met Leu Ala Gly Lys Gly Gly Leu Val Ala His Phe Gly Ile Asn
                245                 250                 255

Asp Ala Arg Val Ile Lys Lys Met Ile Glu Glu Gly Asn Gln Glu Val
```

```
              260                 265                 270
Arg Leu Val Tyr Glu Ala Met Ala Tyr Gln Val Ala Lys Glu Ile Gly
            275                 280                 285

Ala Cys Ala Ala Val Leu Cys Gly Arg Val Asp Ala Val Val Leu Thr
        290                 295                 300

Gly Gly Leu Ala His Asp Glu Met Leu Val Asp Trp Ile Lys Asn Arg
305                 310                 315                 320

Val Ser Phe Ile Ala Pro Val Tyr Val Phe Pro Gly Glu Asp Glu Leu
                325                 330                 335

Arg Ala Leu Ala Glu Gly Ala Leu Arg Val Leu Thr Gly Gln Glu Lys
            340                 345                 350

Pro Lys Glu Tyr Leu
        355

<210> SEQ ID NO 20
<211> LENGTH: 1077
<212> TYPE: DNA
<213> ORGANISM: Thermosediminibacter oceani

<400> SEQUENCE: 20
atggaaaagt ttaggatact cgcaataaac cccggatcca catccacgaa gatctcgatt      60
tttcacggtg aagaagaggt tttcacggaa atatagtcc acgattatga gaattgaag      120 aaattcaaaa atgtcataga acaagaaggc taccgttacg aagcgatatt aaacgctctt     180
gcagccaggg gctatagcct ggatgaaata gacgtggtgg tggccagagg tggcattttg     240
cgtccagtca aagcaggcac ctaccgcata acgacctca tgctggagga cctaaaggat      300
gccgtggccg gagagcatgc ctccaatgtg gctgctttta tagctcatcg catcggtgct     360
gaaaagggta tcccggctta tatagtcgac ccggtttctg tggatgaaat ggaagatgtg     420
gcgcgtattt cggggctcga cggaatcgag agaaagagcc tgtcccacgc gctcaacatc     480
agacgggtta tatataaggt ctctgaaaaa ttcggaaaag acccaggtga gctcaatttc     540
attgtggctc acctgggcgg cgggatttcc ataggtgcca taagaagggg acagatggta     600
gatgtggaga gcgccaactg cgagggcccc ttttccccgg aaaggtcagg ggggctgccg     660
atcctagagc tgatagacct ctgcttcagc ggcaggttta cgaaagatga gctgaaaaga     720
agacttatcc aggaaggcgg ggtatattcg tatctcggaa cgaaggatat aagagaagtt     780
gaagaaagaa caaggagcgg cgataaaaaa gctgccctca tactggaggc gatggtttac     840
caaatagcca gtgtataggc cagatggcg acggtattaa aggcgatgt ggactttata      900 attcttaccg gaggcatagc caaatccgat tacatcagcg aatgtatagc cgacagggtt     960
aaattcatag cccctgtaga aagagtgccc ggcgaagagg atgaaggc actagctgaa     1020 gccgcgtgta gggtcatgac cgggcgcgag aaggtactgg attacggggg aggtgaa       1077

<210> SEQ ID NO 21
<211> LENGTH: 359
<212> TYPE: PRT
<213> ORGANISM: Thermosediminibacter oceani

<400> SEQUENCE: 21

Met Glu Lys Phe Arg Ile Leu Ala Ile Asn Pro Gly Ser Thr Ser Thr
1               5                   10                  15

Lys Ile Ser Ile Phe His Gly Glu Glu Val Phe Thr Glu Asn Ile
            20                  25                  30

Val His Asp Tyr Glu Glu Leu Lys Lys Phe Lys Asn Val Ile Glu Gln
```

```
                35                  40                  45
Glu Gly Tyr Arg Tyr Glu Ala Ile Leu Asn Ala Leu Ala Ala Arg Gly
         50                  55                  60

Tyr Ser Leu Asp Glu Ile Asp Val Val Ala Arg Gly Ile Leu
65                  70                  75                  80

Arg Pro Val Lys Ala Gly Thr Tyr Arg Ile Asn Asp Leu Met Leu Glu
                85                  90                  95

Asp Leu Lys Asp Ala Val Ala Gly Glu His Ala Ser Asn Val Ala Ala
            100                 105                 110

Phe Ile Ala His Arg Ile Gly Ala Glu Lys Gly Ile Pro Ala Tyr Ile
        115                 120                 125

Val Asp Pro Val Ser Val Asp Glu Met Glu Asp Val Ala Arg Ile Ser
    130                 135                 140

Gly Leu Asp Gly Ile Glu Arg Lys Ser Leu Ser His Ala Leu Asn Ile
145                 150                 155                 160

Arg Arg Val Ile Tyr Lys Val Ser Glu Lys Phe Gly Lys Asp Pro Gly
                165                 170                 175

Glu Leu Asn Phe Ile Val Ala His Leu Gly Gly Ile Ser Ile Gly
            180                 185                 190

Ala Ile Arg Arg Gly Gln Met Val Asp Val Glu Ser Ala Asn Cys Glu
        195                 200                 205

Gly Pro Phe Ser Pro Glu Arg Ser Gly Gly Leu Pro Ile Leu Glu Leu
    210                 215                 220

Ile Asp Leu Cys Phe Ser Gly Arg Phe Thr Lys Asp Glu Leu Lys Arg
225                 230                 235                 240

Arg Leu Ile Gln Glu Gly Val Tyr Ser Tyr Leu Gly Thr Lys Asp
                245                 250                 255

Ile Arg Glu Val Glu Glu Arg Thr Arg Ser Gly Asp Lys Lys Ala Ala
            260                 265                 270

Leu Ile Leu Glu Ala Met Val Tyr Gln Ile Ala Lys Cys Ile Gly Gln
        275                 280                 285

Met Ala Thr Val Leu Lys Gly Asp Val Asp Phe Ile Ile Leu Thr Gly
    290                 295                 300

Gly Ile Ala Lys Ser Asp Tyr Ile Ser Glu Cys Ile Ala Asp Arg Val
305                 310                 315                 320

Lys Phe Ile Ala Pro Val Glu Arg Val Pro Gly Glu Glu Met Lys
                325                 330                 335

Ala Leu Ala Glu Ala Ala Cys Arg Val Met Thr Gly Arg Glu Lys Val
            340                 345                 350

Leu Asp Tyr Gly Gly Gly Glu
        355
```

<210> SEQ ID NO 22
<211> LENGTH: 1074
<212> TYPE: DNA
<213> ORGANISM: Natranaerobius thermophiles

<400> SEQUENCE: 22

```
atgaaacaag aacatcgctt gttagtaata aatcctggat ccacctccac aaaaatagct    60
gtctatgaag gtgaaagccc attaattgaa agaaactcg aacattcacc agaggaatta   120
aataagtttc aagacattat agaccaatat gactttagaa agatagtat tctgaacttt   180 ctagatgaac agggcatgaa ctttaataaa ctagatgcag ttgtcgccag aggtgggctg   240
ttaaagccta tctctggtgg tacattcaaa gtgaatgatt tgatggtcga acatctaaga   300
```

```
cagggttatc aaggagagca cgcttccaat ttgggaggta ttatagctaa agaaatatct    360
aatcaacttg atattccagc ctatattgtt gatccagtgg tagttgatga attacaggat    420
attgcacgta tatcagggtt tgagccaatt gaaagaaaaa gcattttcca tgcattaaat    480
cacaaagcag ttgccagaaa agcagcagct caactaggta aaaaatatga agaagctaat    540
ttagtagtag ttcatttagg tggaggtatc tccgtggggg cgcataattg cggtgatgtc    600
atcgatgtta ataatgccct cgatggagaa ggacccttt caccagaacg aagtggtgga    660
ctccctaatg gtgatttagt acgatatata gatgagcaca atttaacctg gaaagaatta    720
aaacgacagt tggttggtaa cggtggacta gtatcttatt tagataccaa tgatggtaaa    780
aaagttcaag agatgataca atcaggcgat gagaaagctg aaaaagtata tgaagccatg    840
atctatcaaa tagctaaaga gataggttcc tgtgctgttg tattaaaagg tgaattagat    900
gctattgtat taactggtgg attagctcat gatgaatatc tagtttctag aatgaaggaa    960
tatattaaat tcttgggtga aattctagtc tttcctggag aagatgagat gcaatccttg   1020
gccgaaggtg gcttaagagt cttaagaaat gaagaaactc cgaaagatta ctct         1074
```

<210> SEQ ID NO 23
<211> LENGTH: 358
<212> TYPE: PRT
<213> ORGANISM: Natranaerobius thermophiles

<400> SEQUENCE: 23

```
Met Lys Gln Glu His Arg Leu Leu Val Ile Asn Pro Gly Ser Thr Ser
1               5                   10                  15

Thr Lys Ile Ala Val Tyr Glu Gly Glu Ser Pro Leu Ile Glu Lys Lys
                20                  25                  30

Leu Glu His Ser Pro Glu Glu Leu Asn Lys Phe Gln Asp Ile Ile Asp
            35                  40                  45

Gln Tyr Asp Phe Arg Lys Asp Ser Ile Leu Asn Phe Leu Asp Glu Gln
        50                  55                  60

Gly Met Asn Phe Asn Lys Leu Asp Ala Val Ala Arg Gly Gly Leu
65                  70                  75                  80

Leu Lys Pro Ile Ser Gly Gly Thr Phe Lys Val Asn Asp Leu Met Val
                85                  90                  95

Glu His Leu Arg Gln Gly Tyr Gln Gly Glu His Ala Ser Asn Leu Gly
            100                 105                 110

Gly Ile Ile Ala Lys Glu Ile Ser Asn Gln Leu Asp Ile Pro Ala Tyr
        115                 120                 125

Ile Val Asp Pro Val Val Asp Glu Leu Gln Asp Ile Ala Arg Ile
    130                 135                 140

Ser Gly Phe Glu Pro Ile Glu Arg Lys Ser Ile Phe His Ala Leu Asn
145                 150                 155                 160

His Lys Ala Val Ala Arg Lys Ala Ala Ala Gln Leu Gly Lys Lys Tyr
                165                 170                 175

Glu Glu Ala Asn Leu Val Val Val His Leu Gly Gly Gly Ile Ser Val
            180                 185                 190

Gly Ala His Asn Cys Gly Asp Val Ile Asp Val Asn Asn Ala Leu Asp
        195                 200                 205

Gly Glu Gly Pro Phe Ser Pro Glu Arg Ser Gly Gly Leu Pro Asn Gly
    210                 215                 220

Asp Leu Val Arg Tyr Ile Asp Glu His Asn Leu Thr Trp Lys Glu Leu
225                 230                 235                 240
```

```
Lys Arg Gln Leu Val Gly Asn Gly Gly Leu Val Ser Tyr Leu Asp Thr
                245                 250                 255

Asn Asp Gly Lys Lys Val Gln Glu Met Ile Gln Ser Gly Asp Glu Lys
            260                 265                 270

Ala Glu Lys Val Tyr Glu Ala Met Ile Tyr Gln Ile Ala Lys Glu Ile
        275                 280                 285

Gly Ser Cys Ala Val Val Leu Lys Gly Glu Leu Asp Ala Ile Val Leu
    290                 295                 300

Thr Gly Gly Leu Ala His Asp Glu Tyr Leu Val Ser Arg Met Lys Glu
305                 310                 315                 320

Tyr Ile Lys Phe Leu Gly Glu Ile Leu Val Phe Pro Gly Glu Asp Glu
                325                 330                 335

Met Gln Ser Leu Ala Glu Gly Gly Leu Arg Val Leu Arg Asn Glu Glu
            340                 345                 350

Thr Pro Lys Asp Tyr Ser
        355

<210> SEQ ID NO 24
<211> LENGTH: 1083
<212> TYPE: DNA
<213> ORGANISM: Symbiobacterium thermophilum

<400> SEQUENCE: 24
atgcagcagc gcctgctgat catcaacccg ggctcaacct ccacgaagat cgccgtgtac      60
gacgacgact cccccctgtt cgccgagacg ctgcgccaca gcgcggccga cctggcgtgt     120
ttccgggacg tcgccgccca gttccccttc cggcgggacc tgatcctgga ggctctcgac     180
gcccacggcg tgtcgctctc ctcgctcacc gccgtggtgg ggcgcggcgg gctcctgcgg     240
cccgtgcgcg ggggaaccta ccgggtggac gcggccatgc tggcggagct ctcccgggct     300
gcccacggcg agcacgcgtc caacctgggc gccctcctcg cccacgagat cgcccaggcc     360
gcgggcggcg tgccggcctt catcgtcgac cccgtggtgg tggacgagct ggagccggtg     420
gccaggctca ccggcctgcc ggagatgccg cggcggtcgg tcttccacgc cctcaaccag     480
aaggcggtgg cgcggcgggc gcggccgac ctggccgcg cctacaccga ggtcaacctg      540
gtcgtcgtcc acctgggcgg cgggatctcg gtggggcgc accggcgcgg cgggtcgtc      600 gacgtcaaca cgcgctgga cggcgagggg ccgatgcgc cggagcgggc aggcacggtg      660
cccagcctgg ggctggtcca cctggcgttc tcctggcagc acacgctgcg ggaggtgggg     720
cggatgctgg tcggccgcgg cggtctggtg gcgcacgtgg gcaccaacga cgcccggcgg     780
gtggaggagc ggatcgccgc gggcgacgag gcagcccggg tcgcgtaccg ggccatggcg     840
taccaggtgg ccaaggaggt gggccggcg cggtggccc tgggcggcca ggtggaccgc     900
atcgtgctga cgggcggact ggcccactcc gagatgctga cgggctggat cgcggagcag     960
gtggagtgga tcgctccggt ggcggtctac cccggcgagg acgagatggc cgcgctggcg    1020
gccggcgccc tgcgggtgct gcggggcgag gagccggcgc aggtgtacgg ggaggcaggc    1080
gag                                                                  1083

<210> SEQ ID NO 25
<211> LENGTH: 361
<212> TYPE: PRT
<213> ORGANISM: Symbiobacterium thermophilum

<400> SEQUENCE: 25
```

```
Met Gln Gln Arg Leu Leu Ile Ile Asn Pro Gly Ser Thr Ser Thr Lys
1               5                   10                  15
Ile Ala Val Tyr Asp Asp Ser Pro Leu Phe Ala Glu Thr Leu Arg
            20                  25                  30
His Ser Ala Ala Asp Leu Ala Cys Phe Arg Asp Val Ala Ala Gln Phe
        35                  40                  45
Pro Phe Arg Arg Asp Leu Ile Leu Glu Ala Leu Asp Ala His Gly Val
    50                  55                  60
Ser Leu Ser Ser Leu Thr Ala Val Val Gly Arg Gly Gly Leu Leu Arg
65                  70                  75                  80
Pro Val Arg Gly Gly Thr Tyr Arg Val Asp Ala Ala Met Leu Ala Glu
                85                  90                  95
Leu Ser Arg Ala Ala His Gly Glu His Ala Ser Asn Leu Gly Ala Leu
            100                 105                 110
Leu Ala His Glu Ile Ala Gln Ala Ala Gly Gly Val Pro Ala Phe Ile
        115                 120                 125
Val Asp Pro Val Val Asp Glu Leu Glu Pro Val Ala Arg Leu Thr
    130                 135                 140
Gly Leu Pro Glu Met Pro Arg Arg Ser Val Phe His Ala Leu Asn Gln
145                 150                 155                 160
Lys Ala Val Ala Arg Arg Ala Ala Asp Leu Gly Arg Ala Tyr Thr
                165                 170                 175
Glu Val Asn Leu Val Val His Leu Gly Gly Ile Ser Val Gly
            180                 185                 190
Ala His Arg Arg Gly Arg Val Val Asp Val Asn Asn Ala Leu Asp Gly
        195                 200                 205
Glu Gly Pro Met Ala Pro Glu Arg Ala Gly Thr Val Pro Ser Leu Gly
    210                 215                 220
Leu Val His Leu Ala Phe Ser Trp Gln His Thr Leu Arg Glu Val Gly
225                 230                 235                 240
Arg Met Leu Val Gly Arg Gly Leu Val Ala His Val Gly Thr Asn
                245                 250                 255
Asp Ala Arg Arg Val Glu Glu Arg Ile Ala Ala Gly Asp Glu Ala Ala
        260                 265                 270
Arg Val Ala Tyr Arg Ala Met Ala Tyr Gln Val Ala Lys Glu Val Gly
    275                 280                 285
Arg Ala Ala Val Ala Leu Gly Gly Gln Val Asp Arg Ile Val Leu Thr
        290                 295                 300
Gly Gly Leu Ala His Ser Glu Met Leu Thr Gly Trp Ile Ala Glu Gln
305                 310                 315                 320
Val Glu Trp Ile Ala Pro Val Ala Val Tyr Pro Gly Glu Asp Glu Met
                325                 330                 335
Ala Ala Leu Ala Ala Gly Ala Leu Arg Val Leu Arg Gly Glu Glu Pro
        340                 345                 350
Ala Gln Val Tyr Gly Glu Ala Gly Glu
            355                 360
```